US009975859B2

(12) United States Patent
Zhang et al.

(10) Patent No.: US 9,975,859 B2
(45) Date of Patent: May 22, 2018

(54) METHOD FOR PREPARING NITROGEN-CONTAINING AROMATIC COMPOUND BY CATALYTIC PYROLYSIS OF ORGANIC MATERIAL

(71) Applicant: UNIVERSITY OF SCIENCE AND TECHNOLOGY OF CHINA, Hefei, Anhui (CN)

(72) Inventors: Ying Zhang, Hefei (CN); Lujiang Xu, Hefei (CN); Qian Yao, Hefei (CN)

(73) Assignee: University of Science and Technology of China, Hefei (CN)

( * ) Notice: Subject to any disclaimer, the term of this patent is extended or adjusted under 35 U.S.C. 154(b) by 0 days. days.

(21) Appl. No.: 15/009,499

(22) Filed: Jan. 28, 2016

(65) Prior Publication Data

US 2016/0145217 A1 May 26, 2016

Related U.S. Application Data

(63) Continuation of application No. PCT/CN2013/080639, filed on Aug. 1, 2013.

(51) Int. Cl.

| | |
|---|---|
| ***C07D 241/12*** | (2006.01) |
| ***C07D 207/32*** | (2006.01) |
| ***C07D 209/08*** | (2006.01) |
| ***C07D 213/16*** | (2006.01) |
| ***C10B 53/02*** | (2006.01) |
| ***C10B 57/06*** | (2006.01) |
| ***C07D 471/04*** | (2006.01) |
| ***C07C 209/00*** | (2006.01) |
| ***B01J 29/76*** | (2006.01) |
| ***C07D 207/323*** | (2006.01) |

(52) U.S. Cl.

CPC ............ *C07D 241/12* (2013.01); *B01J 29/76* (2013.01); *C07C 209/00* (2013.01); *C07D 207/32* (2013.01); *C07D 207/323* (2013.01); *C07D 209/08* (2013.01); *C07D 213/16* (2013.01); *C07D 471/04* (2013.01); *C10B 53/02* (2013.01); *C10B 57/06* (2013.01); *Y02E 50/14* (2013.01); *Y02P 20/145* (2015.11)

(58) Field of Classification Search

CPC .............. C07D 207/323; C07D 209/08; C07D 213/16; C07D 241/12

See application file for complete search history.

(56) References Cited

FOREIGN PATENT DOCUMENTS

| | | | |
|---|---|---|---|
| CN | 1775754 A | | 5/2006 |
| CN | 101475544 A | | 7/2009 |
| CN | 103214392 A | | 7/2013 |
| WO | WO 2013/188404 | * | 12/2013 |

OTHER PUBLICATIONS

Slow catalytic pyrolysis of rapeseed cake: Product yield and characterization of the pyrolysis liquid. Smets et al. Biomass and Bioenergy, 2013, 57, 180-190.*

International Search Report and English Translation of the Written Opinion of the International Searching Authority, dated May 5, 2014, for corresponding International Application No. PCT/CN2013/080639, 12 pages.

* cited by examiner

*Primary Examiner* — Brian McDowell

(74) *Attorney, Agent, or Firm* — Seed IP Law Group LLP

(57) ABSTRACT

Provided is a method for preparing a nitrogen-containing aromatic compound through catalytic pyrolysis from organic materials. The method comprises: feeding organic materials and a catalyst into a reactor, to enable the organic material to undergo reactions in the presence of nitrogen and under heating conditions, so as to generate a reaction system flow containing one or more nitrogen-containing aromatic compounds.

19 Claims, 4 Drawing Sheets

Pyrazine compounds and pyrrole compounds

Indole compounds

Aniline and indole compounds

Pyridine and pyrrole compounds

METHOD FOR PREPARING NITROGEN-CONTAINING AROMATIC COMPOUND BY CATALYTIC PYROLYSIS OF ORGANIC MATERIAL

TECHNICAL FIELD

This invention generally relates to a method for preparing a nitrogen-containing aromatic compound by catalytic pyrolysis of an organic material, and specifically, to a method for preparing pyrazine compounds, pyridine compounds, pyrrole compounds, indole compounds, aniline compounds or a combination thereof by catalytic pyrolysis of biomass.

BACKGROUND ART

Biomass carbohydrates are an important class of organic compounds which are most abundant and widest distributed in the planet, and are mainly composed of carbon, hydrogen, and oxygen. Glucose, sucrose, starch, cellulose, and so on all belong to carbohydrates. As the problems of consumption and pollution of coal and petroleum resources are more and more severe globally, the demand for seeking a renewable and clean energy is more and more urgent. Compared to fossil energy sources, the biomass energy sources have the features of wide distribution, large total amount, no pollution, and good renewability. In addition, wastes, such as waste proteins, municipal organic refuse, and the like, are discarded in a large amount without effective utilization, resulting in serious resource waste and environmental pollution. The biomass resource is the only sustainable source of organic carbon and the only renewable resource which may be converted to liquid fuel. The preparation of chemicals with high values starting from biomass also becomes more and more important.

Biomass pyrolysis, particularly fast pyrolysis, may obtain liquid fuels and chemicals with high values, which is considered as one of the most effective method for utilizing the biomass. Catalytic fast pyrolysis allows targeted pyrolysis of biomass with catalyst added so as to improve the yield of one or more products.

Pyrazine is a six-membered heterocyclic compound which contains two nitrogen heteroatoms at 1-, and 4-positions, and has the molecular formula of $C_4H_4N_2$. The one in which two nitrogen atoms occupy 1-, and 2-positions is referred to as pyridazine, and the one in which two nitrogen atoms occupy 1-, and 3-positions is referred to as pyrimidine, both of which are isomers of pyrazine. Pyrazine is a colorless crystal with a melting point of 54° C., a boiling point of 115-116° C., and a liquid-state relative density of 1.0311 (61/4° C.). It has similar odor with pyridine and is soluble in water, ethanol, ethyl ether, etc. Pyrazine is a very weak base. Its aromaticity is similar to that of pyridine and is not prone to subject to electrophilic substitution reaction, whereas it is relatively active to nucleophilic reagents. After a hydrogen atom on a carbon atom is substituted with a methyl group or a halogen atom, the halogen atom or the hydrogen on the methyl group is active. Pyrazine compounds may be used as important medical intermediates and intermediates of fragrances and flavors, and are also a kind of fine chemicals with high values. The derivatives thereof have many applications, for example, the citrate of hexahydropyrazine (or referred to as piperazine) is a commonly-used livestock antihelmintic and is particularly effective to ascarid; 2-methylpyrazine is an important medical intermediate and may be used to prepare pyrazinamide, which is an antituberculosis drug; 2-methylpyrazine-5-carboxylic acid may be used to prepare drugs having functions of reducing blood sugar, reducing blood pressure, and so on; 2,5-diketopiperazine is an agent for preparing peptide compounds; dibenzopyrazine is an important dye, and phenazine is well known for having antitumoral, antibacterial, and diuretic properties. Furthermore, it is reported that tetramethylpyrazine may capture superoxide anions and reduce the generation of nitrogen oxides in granulocytes of human bodies. Pyridine and alkyl pyridine are six-membered cyclic compounds containing one nitrogen atom, and typically, pyridine and derivatives thereof are collectively called pyridine base compounds, which mainly include pyridine, 2-methylpyridine, 3-methylpyridine, 4-methylpyridine, etc. Pyridine and derivatives are very important chemical intermediates and are widely used in industries of medicines, pesticides, fodders, synthetic rubbers and printing and dyeing, and may also be used in the production of surfactants and food additives. Pyridine is mainly industrially used for producing sulfonamide, penicillin, vitamin A, cortisone, antihelmintics, local anesthetics, etc, and may also be used for stabilizers, softening agents, paint solvent, condensation agents of synthetic resins as well as used for synthesizing herbicides, preservatives, hydroxypyridine, etc. 2-methylpyridine may be used for producing 2-ethylpyridine, which is an important raw material of the synthetic rubber industry, and is also used for preparing amprolium, long-lasting sulfonamide, cathartics and film photoresist additives in medical industry, as well as raw materials of resins and fuel intermediates, etc. 3-methylpyridine may be used for preparing vitamin B, nikethamide, cardiotonics, pesticides, waterproofing agents, etc, and the important application thereof is the production of nicotinic acid and nicotinamide which are useful as additives of the fodder industry. 4-methylpyridine is mainly used as raw material and solvent for organic synthesis, and may also be used for preparing isoniazid, which is a drug for treating tuberculosis, and also a raw material for preparing dyes, pesticides, catalysts, rubber vulcanization accelerators, and synthetic resins. As the demand for pyridine derivatives increases, the method of recovering and separating pyridine and derivatives from coking byproducts is difficult to satisfy the market demand. Chichibabin has proposed a process scheme for producing pyridine and derivatives using aldehyde and ammonia as raw materials. However, they are mainly derived from the petrochemical industry. Pyrrole compounds are widely present in metabolites of plants, animals and microorganisms. Pyrrole and alkyl pyrroles are five-membered nitrogen-containing heterocyclic compounds, and a number of natural and synthetic multi-substituted pyrrole compounds often have antibacterial, anti-inflammatory, and analgesic functions. As important intermediates of fine chemical products, pyrrole compounds have wide application in the fields of medicines, foods, pesticides, commodity chemicals, coatings, weaving, printing, paper making, photosensitive materials, polymer materials, etc. For example, pyrrole may be used to synthesize porphobilinogen having bioactivity, pyoluteorin having antimicrobial activity, N-methyl-2-acetylpyrrole, a barbecue-flavored fragrance 2-acetylpyrrole, etc. In recent years, pyrrole has been also used in the field of electrically conductive polymers and the demand therefor is increasing. The raw materials for the industrial production of pyrrole compounds are mainly derived from petrochemical products. Indole is an essential chemical raw material and is widely used in various fields of medicines, pesticides, dyes, foods, flavors, etc. In recent years, downstream products of indole have been rapidly developed and new fields of application continuously derive, such as a number of important drugs and pesticides. Particularly, the increasing demand for tryptophan, which is a derivative of indole, leads to great increase of the demand for indole in the world. Indole has a very wide market prospect. At present, indole is industrially synthesized mainly by a one-step heterogeneous catalysis method using aniline and ethylene glycol as raw materials. Aniline is an important industrial chemical and may be used as raw material for producing rubber vulcanization accelerator, dye, mordant, drug, explosive and methylene diphenyl diisocyanate (MDI). When alkyl-substituted anilines, such as toluidine, cumidine, methylcumidine, dimethylaniline and diisopropylaniline, are used as raw materials, the application of developers, agricultural agents, and drugs may be improved. In recent years, the usage amount of aniline has continuously increased, and the demand in China has increased from 340 thousand t/a to 2065 thousand t/a. The global usage amount of aniline is much more. It is estimated that the global consumption amount of aniline will be up to 6500 thousand t/a by 2015. Nowadays, main production methods of aniline are nitrobenzene catalytic hydrogenation method, phenol amination method, and nitrobenzene iron powder reduction method, wherein 90% of aniline is produced by nitrobenzene catalytic hydrogenation method. The production method using an aromatic nitro compound requires consumption of a large amount of sulfuric acid or nitric acid as a nitrification agent of aromatic compounds. Next, the neutralization reaction requires a large amount of base. In addition, nitrogen oxide gas will generate when the nitro compound is formed, which results in air pollution.

SUMMARY

This disclosure relates to a method for selectively preparing pyrazine, pyridine, pyrrole, indole, and aniline compounds by catalytic pyrolysis of various biomass and derivatives as well as agriculture, forestry, and municipal wastes, by means of regulation of catalysts and reaction conditions.

More specifically, the present disclosure relates to catalytic pyrolysis of an organic material in the presence of a nitrogen-containing gas. In one embodiment of the invention, the organic material comprises agricultural and municipal solid waste, food waste, animal waste, carbohydrates, lignocellulose, and the like, or a combination thereof. In one embodiment of this invention, the organic material comprises wood, bagasse, bamboo, corn straws, waste paper, rapeseed meal, Jatropha curcas meal, soybean meal, lee, waste protein, microalgae or a combination thereof. In one embodiment of this invention, the organic material comprises glucose, cellobiose, cellulose, starch, xylose, xylitol, xylan, chitosan, chitin, sucrose, fructose, aqueous glucose solution, methylfuran, 2,5-dimethylfuran, furfural, 5-hydroxymethylfurfural, 5-methylfurfural, γ-valerolactone, cellulose bio-oils, water-soluble bio-oils, water-insoluble bio-oils, and the like, or a combination thereof.

A method for preparing a nitrogen-containing aromatic compound by catalytic pyrolysis of an organic material, comprising: feeding an organic material and a catalyst to a reactor; and reacting the organic material feed with catalyst in the presence of a nitrogen-containing gas and under heating conditions in the reactor, to generate a reaction stream comprising one or more nitrogen-containing aromatic compounds. In one embodiment of this invention, in the separation of at least a part of the nitrogen-containing aromatic compounds in the reaction stream, in addition to the product stream comprising the separated nitrogen-containing aromatic compounds, a recycle stream is also obtained; and at least a part of the recycle stream is fed to the reactor.

In one embodiment of this invention, the nitrogen-containing gas comprises $NH_3$, an organic amine such as methylamine, dimethylamine and ethylamine, and/or an inert gas. In one embodiment of this invention, the nitrogen-containing gas comprises $NH_3$ and an inert gas with a molar ratio greater than about 1:19. In one embodiment of this invention, the nitrogen-containing gas comprises $NH_3$ and $N_2$ with a molar ratio of about 1:19, 1:9, 1:4, 1:1, 4:1, 19:1, 1:0, etc.

In one embodiment of this invention, the nitrogen-containing aromatic compound comprises pyrazine compounds, pyridine compounds, pyrrole compounds, indole compounds, aniline compounds, and the like, or a combination thereof. In one embodiment of this invention, pyrazine compounds include pyrazine, 2-methylpyrazine, 2,5-dimethylpyrazine, 2,6-dimethylpyrazine, and the like; pyridine compounds include pyridine, 2-methylpyridine, 3-methylpyridine, 4-methylpyridine, dimethylpyridine, and the like; pyrrole compounds include pyrrole, 2-methylpyrrole, 3-methylpyrrole, 2,5-dimethylpyrrole, and the like; indole compounds include indole, 1-methylindole, 2-methylindole, 3-methylindole, 2,8-dimethylindole, and the like; and aniline compounds include aniline, o-methylaniline, m-methylaniline, p-methylaniline, dimethylaniline, and the like. In one embodiment of this invention, the catalyst comprises one or more of a zeolite catalyst, a non-zeolite catalyst, a metal catalyst and/or a metal oxide catalyst, etc.

In one embodiment of this invention, the catalyst comprises γ-$Al_2O_3$, $SiO_2$—$Al_2O_3$, $WO_3/ZrO_2$, $SO_4^{2}/ZrO_2$, MCM-41, ZK-5, ZSM-23, SSZ-20, β-zeolite, Y-zeolite, ZSM-5 and/or HZSM-5, etc. In one embodiment of this invention, the catalyst has a $SiO_2/Al_2O_3$ ratio of 15:1 to 200:1, such as a $SiO_2/Al_2O_3$ ratio of 15:1, 25:1, 50:1, 63:1, 80:1, 100:1, 150:1 or 200:1, etc.; In one embodiment of this invention, the mass ratio of the catalyst to the organic material is 1:100 to 100:1, such as 1:100, 1:50, 1:20, 1:15, 1:10, 1:5, 1:2, 1:1, 2:1, 5:1, 10:1, 15:1, 20:1, 50:1, 100:1, etc.

In one embodiment of this invention, the mass ratio of the catalyst to the organic material is 0.1:1 to 10:1, and the nitrogen-containing aromatic compound is a pyrrole compound and/or a pyrazine compound. In one embodiment of this invention, the mass ratio of the catalyst to the organic material is 5:1 to 20:1, and the nitrogen-containing aromatic compound is an indole compound. In one embodiment of this invention, the catalyst performs catalysis by a plurality of catalyst granules, and granules whose largest cross-sectional sizes are less than about 1 micrometer comprise at least about 50% of the total volume of the catalyst. In one embodiment of this invention, the catalyst has pores of about 5 Angstroms to about 100 Angstroms. In one embodiment of this invention, the catalyst comprises a plurality of pores; at least about 95% of pores of one or more catalysts have smallest cross-sectional diameters that lie within a first size distribution and a second size distribution; at least 5% of pores have smallest cross-sectional diameters that lie within the first size distribution; at least about 5% of pores have smallest cross-sectional diameters that lie within the second size distribution; the first size distribution and the second size distribution do not overlap. It may be desirable, in some embodiments, to employ one or more catalysts to establish a bimodal distribution of pore sizes. In some cases, a single catalyst with a bimodal distribution of pore sizes may be used. In some other cases, a mixture of two or more catalysts may be used to establish a bimodal distribution. In some embodiments, one of the one or more catalysts comprises a zeolite catalyst and another of the one or more catalysts comprises a non-zeolite catalyst.

In some embodiments, at least about 70%, at least about 80%, at least about 90%, at least about 95%, at least about 98%, or at least about 99% of the pores of the one or more catalysts have smallest cross-sectional diameters that lie within a first size distribution or a second size distribution. In some cases, at least about 2%, at least about 5%, or at least about 10% of the pores of the one or more catalysts have smallest cross-sectional diameters that lie within the first size distribution; and at least about 2%, at least about 5%, or at least about 10% of the pores of the one or more catalysts have smallest cross-sectional diameters that lie within the second size distribution. In some cases, the first and second size distributions are selected from the ranges provided above.

In one embodiment of this invention, the catalyst contains one or more of the following doping metals: Cu, Mn, Co, Fe, Ni, Zn, Ga, Pt, In, Ru, Rh, Ir, Pt, Pd, Au, Re, Tl and lanthanide metals, and the like. In one embodiment of this invention, the doping metal is doped into the catalyst by means of dry/wet impregnation or ion exchange. In one embodiment of this invention, the catalyst is HZMS-5 and the nitrogen-containing aromatic compound is a pyrrole compound. In one embodiment of this invention, the catalyst is $SO_4^{2-}/ZrO_2$ and the nitrogen-containing aromatic compound is a pyrazine compound.

In one embodiment of this invention, the reaction temperature in the reactor is 300° C. to 800° C., such as 300° C., 400° C., 500° C., 600° C., 700° C., 800° C., etc. In one embodiment of this invention, the reaction temperature in the reactor is 300° C. to 500° C., and the nitrogen-containing aromatic compound is a pyrrole compound. In one embodiment of this invention, the reaction temperature in the reactor is 500° C. to 800° C., preferably 600° C., and the nitrogen-containing aromatic compound is an indole compound and/or an aniline compound. In one embodiment of this invention, the reactor is a fixed bed reactor and/or a fluidized bed reactor, and the like. In one embodiment of this invention, the reactor is a circulating fluidized bed reactor and/or a turbulent fluidized bed reactor, and the like. In one embodiment of this invention, the organic material is fed into the reactor with a weight hourly space velocity (WHSV) of 0.05 to 2, such as a WHSV of 0.05, 0.1, 0.2, 0.5, 0.8, 1, 1.5, 2. In one embodiment of this invention, the organic material is fed into the reactor with a WHSV of 0.8 to 2, and the nitrogen-containing aromatic compound is a pyrrole compound. In one embodiment of this invention, the organic material is fed into the reactor with a WHSV of 0.1 to 0.8, and the nitrogen-containing aromatic compound is an indole compound and/or an aniline compound.

For the first time, the inventors have developed a new pathway of selectively converting biomass, bio-oil and biomass-based chemicals to bulk and fine chemicals in the petrochemical industry, such as pyrazines, pyrroles, pyridines, indoles and anilines by using a catalytic pyrolysis method, and regulating factors such as the type and amount of catalyst, reaction temperature, etc. Compared to methods in the prior art, this invention mainly overcomes the following disadvantages in previous processes for producing these chemicals, for example, (1) the raw materials of this invention are all renewable resources encompassing all biomass materials, while the previous raw materials of the products are derived from petrochemical products; (2) the production process of this invention is a "green" production process and will not have drawbacks in the previous processes of production such as the requirement of a large amount of acid and base, environmental pollution, etc.; (3) when bio-oils or biomass-based chemicals are used as raw materials, this pathway may be similar to or may completely replace reaction pathways in the petrochemical industry; and (4) in this pathway, the whole process from the raw material to the production process step is a renewable, green and environment-friendly pathway.

DESCRIPTION OF EMBODIMENTS

Figure 1A:
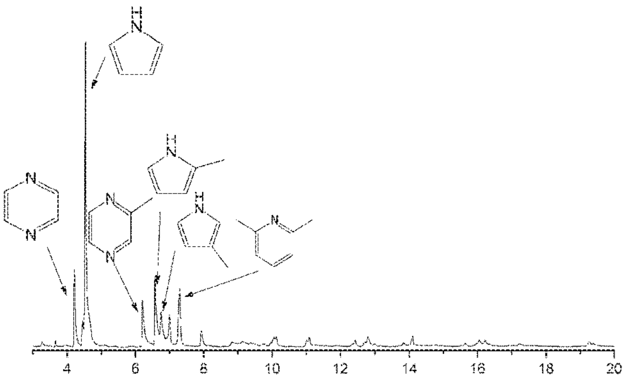
FIGS. 1*a*-1*e* shows gas chromatography-mass spectra and mass spectra of pyrazine and pyrrole compounds prepared by catalytic pyrolysis.
Figure 1B:
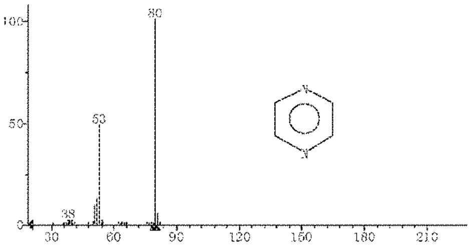
Figure 1C:
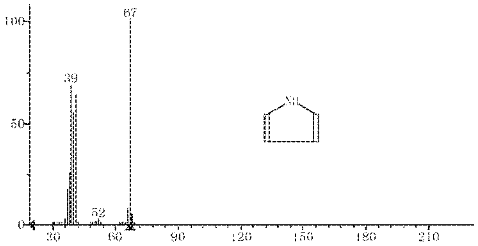
Figure 1D:
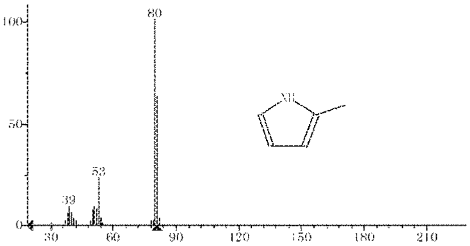
Figure 1E:
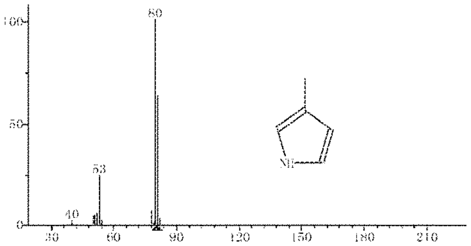
Figure 2A:
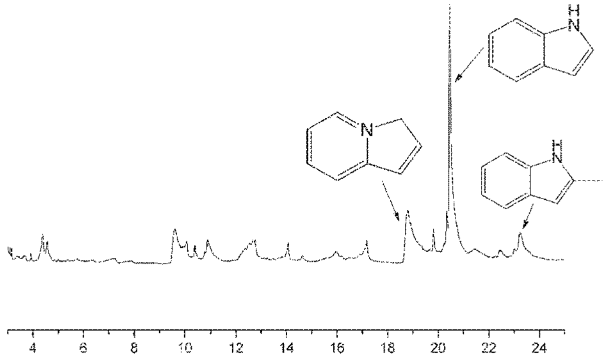
FIGS. 2*a*-2*d* shows gas chromatography-mass spectra and mass spectra of indole compounds prepared by catalytic pyrolysis.
Figure 2B:
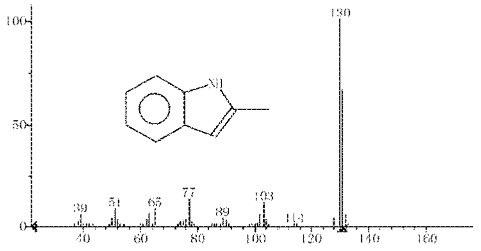
Figure 2C:
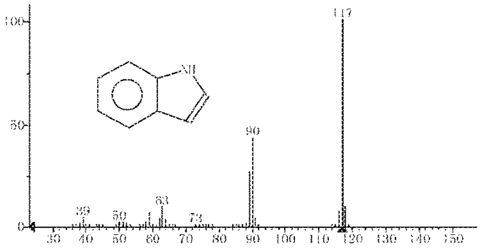
Figure 2D:
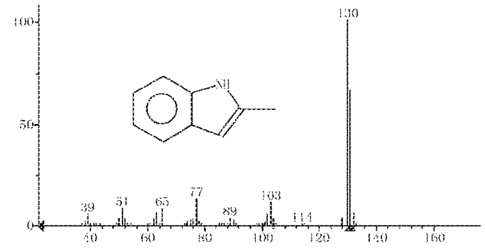
Figure 3A:
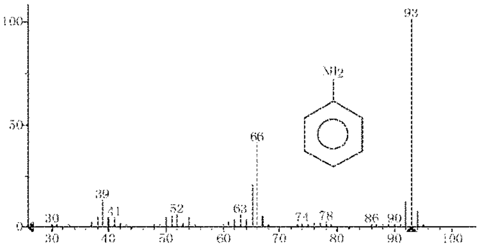
FIGS. 3*a*-3*b* shows gas chromatography-mass spectra and mass spectra of aniline and indole compounds prepared by catalytic pyrolysis.
Figure 3B:
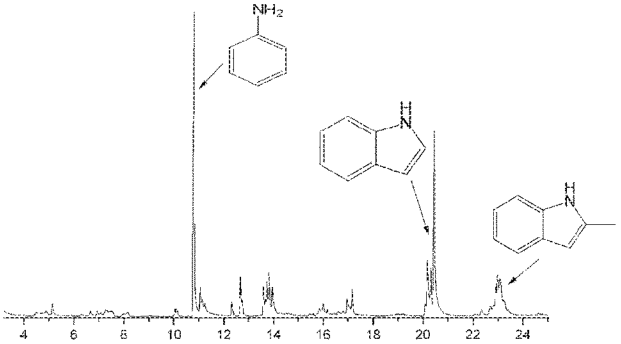
Figure 4A:
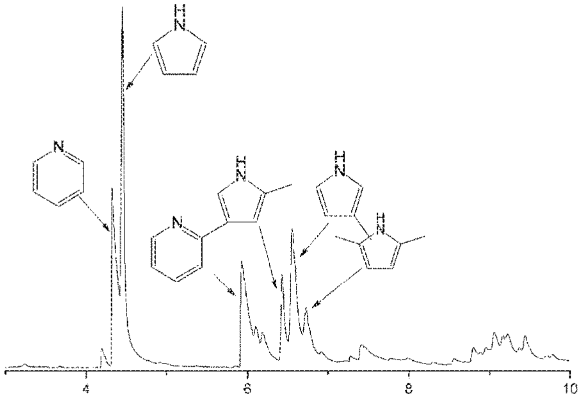
FIGS. 4*a*-4*f* shows gas chromatography-mass spectra and of mass spectra of pyridine and pyrrole compounds prepared by catalytic pyrolysis.
Figure 4B:
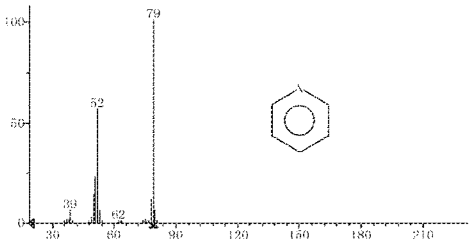
Figure 4C:
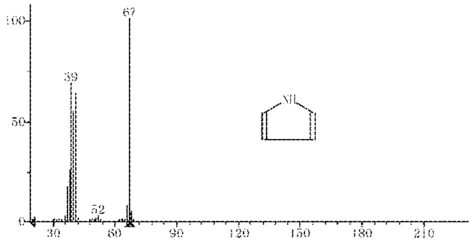
Figure 4D:
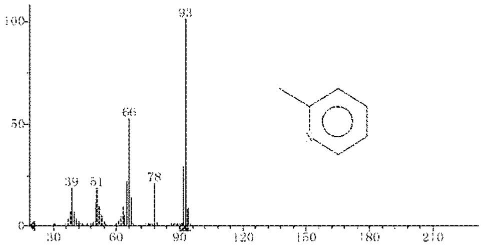
Figure 4E:
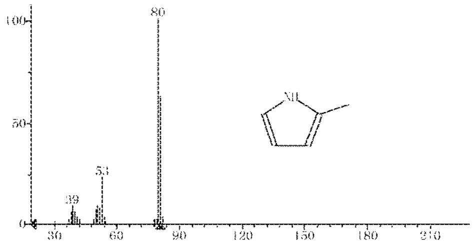
Figure 4F:
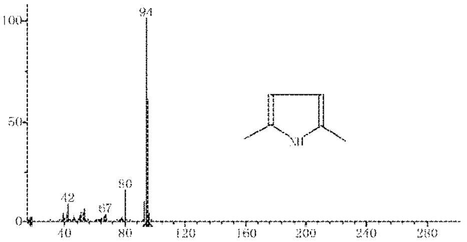

The specification discloses compositions and methods for the preparation of nitrogen-containing aromatic chemicals such as pyrazines, pyridines, pyrroles, indoles, anilines, etc., and more specifically, compositions and methods for the preparation of chemicals via catalytic pyrolysis. Some embodiments relate to methods for the production of fluid (e.g., a liquid, a supercritical fluid, and/or a gas) products, for example nitrogen-containing aromatic chemicals (e.g., pyrazine, pyrrole, indole, aniline, etc) via catalytic pyrolysis processes (e.g., catalytic fast pyrolysis). In certain embodiments, the products or a portion thereof are liquids at standard ambient temperature and pressure (SATP, i.e. 25° C. and 100 kPa absolute pressure). Some of such methods may involve the use of a composition comprising a mixture of an organic material, for example a liquid, gaseous and/or solid organic material, and a heterogeneous pyrolytic catalyst component. In some embodiments, the organic material can be fed to a reactor, undergo catalytic pyrolysis, and a portion the product stream can be recycled to the feed stream comprising the organic material.

In some embodiments of the invention, the products which may be generated are as shown in Table 1.

TABLE 1

Compound name and boiling point of the products of the invention

| Compound Name | Boiling Point (° C.) |
|---|---|
| pyrrole | 131 |
| 3-methylpyrrole | 144 |
| pyridine | 115.3 |
| 3-methylpyridine | 144 |
| pyrazine | 115-116 |
| 2,5-dimethyl pyrazine | 155 |
| indole | 253-254 |
| N-methylindole | 271 |
| 2-methylindole | 273 |
| 2,8-dimethylindole | — |
| aniline | 184 |
| 3-methylaniline | 203-204 |
| 2-methylpyrrole | 147 |
| 2,5-dimethylpyrrole | — |
| 2-methylpyridine | 128-129 |
| 4-methylpyridine | 145 |
| 2-methylpyrazine | 135 |
| 2,6-dimethylpyrazine | 154 |
| indolizine | — |
| methylindole | — |
| 3-methylindole | 265-266 |
| 3,8-dimethylindole | — |
| 2-methylaniline | 199-200 |
| 4-methylaniline | 200 |

In some embodiments, the mixture may be pyrolyzed at high temperatures (e.g., 300° C. to 800° C.). The process of pyrolysis requires at least a time sufficient for generating partially separable and recognizable nitrogen-containing aromatic product fluid. The methods described herein may also involve the use of specialized catalysts. For example, in some cases, zeolite catalysts are used; optionally, the catalysts used herein may have arbitrary silica to alumina molar ratios. The catalyst can, in some cases, be formed of or comprise relatively small particles, which may be agglomerated. In some instances, the composition fed to the pyrolysis reactor has an arbitrary catalyst to organic material mass ratio.

Some embodiments can be directed to a single-stage method for the pyrolysis of biomass. Such a method can comprise providing or using a single-stage pyrolysis apparatus. A single-stage pyrolysis apparatus is one in which pyrolysis and subsequent catalytic reactions are carried out in a single vessel. In some embodiments, the single-stage pyrolysis apparatus comprises a fluidized bed reactor. Multi-stage apparatuses can also be used for the production of fluid nitrogen-containing aromatic chemicals, as described in more detail below.

As used herein, the terms "pyrolysis" and "pyrolyzing" are given their conventional meaning in the art and are used to refer to the transformation of a compound (e.g., an organic material) into one or more other substances (e.g., volatile organic compounds, gases and coke) by heat alone without oxidation, which may take place with or without the use of a catalyst. "Catalytic pyrolysis" refers to pyrolysis performed in the presence of a catalyst, and may involve steps as described in more detail below. Example of catalytic pyrolysis processes are outlined, for example, in Huber, G. W. et al, "Synthesis of Transportation Fuels from Biomass: Chemistry, Catalysts, and Engineering" Chem. Rev. 106, (2006), pp. 4044-4098, which is incorporated herein by reference in its entirety. As used herein, the term "biomass" is given its conventional meaning in the art and is used to refer to any organic source of energy or chemicals that is renewable. Its major components can be (1) trees (wood) and all other vegetation; (2) agricultural products and wastes; (3) algae and other marine plants; (4) metabolic wastes (manure, sewage); and (5) cellulosic urban waste. Examples of biomass materials are described, for example, in Huber, G. W. et al, "Synthesis of Transportation Fuels from Biomass: Chemistry, Catalysts, and Engineering" Chem. Rev. 106, (2006), pp. 4044-4098.

The inventors have discovered that for some reactions, certain changes in reaction conditions and a combination of such changes can produce favorable products and/or yields, lower yields of coke formation and/or more controlled product formation. For example, the use of elevated temperatures (e.g., in the reactor and/or the solids separator) may produce favorable products and/or yields from reactions that may not occur at lower temperatures. Also, the inventors have found that desirable yields of products of indole and aniline compounds can be produced by providing a feed with a high mass ratio of catalyst to organic material. For example, without wishing to be bound by theory, the inventors believe that high heating rates and high catalyst-to-feed mass ratios may facilitate introduction of volatile organic compounds, formed from pyrolysis of the organic feed, into the catalyst before they are thermally decomposed, thus leading to high yields of nitrogen-containing aromatic compounds. Relatively low weight hourly space velocities have also shown to produce desirable yields of nitrogen-containing aromatic compounds. The inventors have also discovered that relatively long residence times of organic materials in high-temperature components (e.g., the reactor and/or the solids separator) of the system may allow adequate time for additional chemical reactions to form desirable products.

The inventors have also discovered herein that the use of catalysts with specific properties are useful in forming a relatively large amount of nitrogen-containing aromatic compound products. For example, in some cases, the use of catalysts comprising particles of relatively small sizes may result in the production of a relatively high amount of nitrogen-containing aromatic compounds and/or a relatively low amount of coke. As another example, in certain embodiments, ZSM-5 is found to preferentially produce nitrogen-containing aromatic compounds. Additionally, certain catalysts that include Bronsted acid sites and/or well-ordered pore structures are found to selectively produce nitrogen-containing aromatic compounds in some cases. Catalyst pore size may also be used, in some cases, to affect the amounts and types of product compounds produced. The embodiments described herein also involve chemical process designs used to perform catalytic pyrolysis. In some cases, the processes may involve the use of one or more fluidized bed reactors (e.g., a circulating fluidized bed reactor, turbulent fluidized bed reactor, bubbling fluidized bed reactor, etc.). The process designs described herein may optionally involve specialized handling of the material fed to one or more reactors. For example, in some embodiments, the feed material may be dried, cooled, and/or ground prior to supplying the material to a reactor. Other aspects of the invention relate to product compositions produced using the process designs described herein.

Without being bound to a particular mode of action or order of steps of the overall thermal/catalytic conversion process, the inventors believe that catalytic pyrolysis involves partial pyrolysis of organic material (e.g., solid biomass) to produce one or more pyrolysis products (e.g., volatile organics, gases, solid coke, etc.) and at least allow a catalytic reaction of one or more pyrolysis products in a portion of the product fluid under the condition of catalyst. The catalytic reaction may involve volatile organics entering into a catalyst (e.g., a zeolite catalyst) where they are converted to chemicals (e.g., nitrogen-containing aromatic compounds and olefins), in addition to carbon monoxide, carbon dioxide, water, and coke. Inside or upon contact with the catalyst, the biomass-derived species may undergo a series of dehydration, amination, decarbonylation, decarboxylation, isomerization, and dehydrogenation reactions to generate nitrogen-containing aromatic compounds, olefins, CO, $CO_2$ and water. A challenge with selective nitrogen-containing aromatic compounds production is the capability of maximizing the yield of carbon. Issues of fuel production can be addressed by utilizing the methods and processes described herein. For instance, nitrogen-containing aromatics compounds can be controllably produced from organic material feeds by controlling a variety of process parameters including, for example, catalyst selection (including type and physical properties, e.g., pore size, particle size, existence and degree of agglomeration, particle/agglomerate shape, etc.), organic material selection, recycle stream composition, reaction temperature, catalyst to organic mass ratios (e.g., in the feed stream, in the reactor, etc.), silica to alumina molar ratios in catalysts, weight hourly space velocities, residence times in various processing components. Process parameters may be selected such that coke formation rates are relatively low.

In some embodiments, the chemical process of the reaction of organic materials is included. The process may involve, in some embodiments, pyrolyzing in a reactor (e.g., a fluidized bed reactor) at least a portion of an organic material under reaction conditions sufficient to produce one or more pyrolysis products. In addition, the process may involve catalytically reacting at least a portion of the one or more pyrolysis products using a catalyst under reaction conditions sufficient to produce one or more fluid products. In some embodiments, one or more fluid products may be produced from said pyrolysis products by dehydration, amination, decarbonylation, decarboxylation, isomerization, and dehydrogenation reactions; the pyrolysis and catalytic reaction processes may occur in a single reactor. The chemical processes may be used, in some cases, for the production of specific fluid product (e.g., nitrogen-containing aromatic compounds and/or olefins); moreover, a portion of the olefins produced by the chemical process may be recycled into the feed stream via which the organic material is fed to the reactor (e.g., the pyrolysis reactor).

Figure 7:
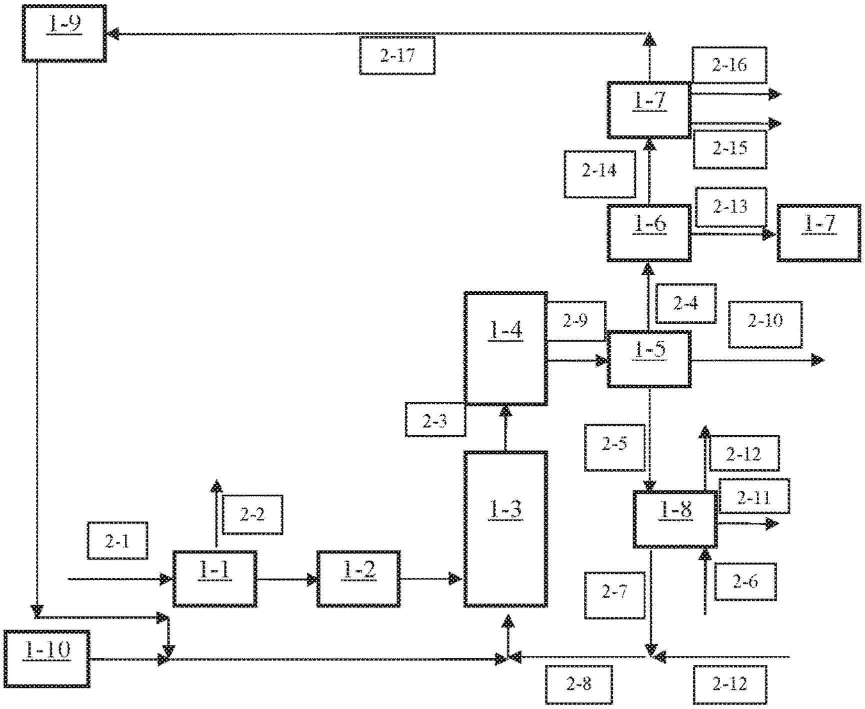
FIG. 7 is a process flow chart of one embodiment of this invention, wherein series 1 is equipment: 1-1: dryer; 1-2: grinding system; 1-3: reactor; 1-4: product reactor; 1-5: solids separator; 1-6: condensation system; 1-7: vapor recovery system; 1-8: catalyst regenerator; 1-9: compression system; 1-10: fluid source. Series 2 is a fluid pathway graph: 2-1: feed composition, which includes biomass, catalyst and carrier gas; and may be solid, liquid and/or gas; 2-2: moisture; 2-3: reaction product stream; 2-4: product stream after separating catalyst; 2-5: separated catalyst stream; 2-6: oxidizing agent, which may include oxygen, air, steam; 2-7: regenerated catalyst stream; 2-8: catalyst recycle stream; 2-9: product stream with product reacted; 2-10: separator purge stream; 2-11: catalyst regenerator purge stream; 2-12: regenerator vent stream; 2-13: liquid component stream of the product; 2-14: gas component stream of the product; 2-15: vapor stream; 2-16: vapor stream of CO, $CO_2$ or other non-recoverable gases; 2-17: other products, such as additional gases.

FIG. 7 includes a schematic illustration of an exemplary chemical process design used to perform catalytic pyrolysis, according to one set of embodiments. In some embodiments, such a process can be used to perform catalytic pyrolysis. As shown in the illustrative embodiment of FIG. 7, a feed stream 2-1 includes a feed composition of the organic material that will be fed to a reactor 1-3. The organic material may generally comprise carbon, hydrogen, oxygen, in which carbon is the most abundant component by mass, as well as minor proportions of other elements such as nitrogen and sulfur. The organic material in the feed composition may comprise a solid, liquid, and/or gas. Specific examples of organic material are provided below.

In some embodiments, the feed composition (e.g., in feed stream 2-1 of FIG. 7) comprises a mixture of an organic material and a catalyst. The mixture may comprise, for example, solids, liquids, and/or gases. In certain embodiments, the mixture comprises a composition of a solid catalyst and a solid organic material. In other embodiments, a catalyst may be provided separately from the feed composition. A variety of catalysts can be used, as described in more detail below. For example, zeolite catalysts with varying molar ratios of silica to alumina and/or varying pore sizes may be used. In some embodiments, for example when a solid organic material is used, moisture 2-2 may optionally be removed from the feed composition prior to being fed to the reactor, e.g., by an optional dryer 1-1. Removal of moisture from the feed stream is advantageous for several reasons. For example, the moisture in the feed stream may require additional energy input in order to heat the feed to a temperature sufficiently high to achieve pyrolysis; variations in the moisture content of the feed may lead to difficulties in controlling the temperature of the reactor; in addition, removal of moisture from the feed can reduce or eliminate the need to process the water during later processing steps. In some embodiments, the feed composition may be dried until the feed composition comprises less than about 10%, less than about 5%, less than about 2%, or less than about 1% water by weight. Suitable equipment capable of removing water from the feed composition is known to those skilled in the art. As an example, in one set of embodiments, the dryer comprises an oven heated to a particular temperature (e.g., at least about 80° C., at least about 100° C., at least about 150° C., or higher) through which the feed composition is continuously, semi-continuously, or periodically passed. In some cases, the dryer may comprise a vacuum chamber into which the feed composition is processed as a batch. Other embodiments of the dryer may combine elevated temperatures with vacuum operation. The dryer may be integrally connected to the reactor or may be provided as a separate unit from the reactor.

In some instances, the particle size of the feed composition may be reduced in an optional grinding system 1-2 prior to passing the feed to the reactor. In some embodiments, the average diameter of the ground feed composition exiting the grinding system may be no more than about 50%, no more than about 25%, no more than about 10%, no more than about 5%, or no more than about 2% of the average diameter of the feed composition fed to the grinding system. Large-particle feed material may be more easily transportable than small-particle feed material. In some cases it may be advantageous to feed small particles to the reactor. The use of a grinding system may allow for the transport of large-particle feed between the source and the production process, while enabling the feed of small particles to the reactor. Suitable equipment capable of grinding the feed composition is known to those skilled in the art. For example, the grinding system may comprise an industrial mill (e.g., hammer mill, ball mill, etc.), a unit with blades (e.g., chipper, shredder, etc.), or any other suitable type of grinding system. In some embodiments, the grinding system may comprise a cooling system (e.g., an active cooling systems such as a pumped fluid heat exchanger, a passive cooling system such as one including fins, etc.), which may be used to maintain the feed composition at relatively low temperatures (e.g., ambient temperature) prior to introducing the feed composition to the reactor. The grinding system may be integrally connected to the reactor or may be provided as a separate unit from the reactor. While the grinding step is shown following the drying step in FIG. 7, the order of these operations may be reversed in some embodiments. In still other embodiments, the drying and grinding steps may be achieved using an integrated unit.

In some cases, grinding and cooling of the organic material may be achieved using separated units. Cooling of the organic material may be desirable, for example, to reduce or prevent unwanted decomposition of the feed material prior to passing it to the reactor. In one set of embodiments, the organic material may be fed into a grinding system to produce a ground organic material. The ground organic material may then be fed from the grinding system to a cooling system to be cooled therein. The organic material may be cooled to a temperature of lower than about 300° C., lower than about 200° C., lower than about 100° C., lower than about 75° C., lower than about 50° C., lower than about 35° C., or lower than about 20° C. prior to introducing the organic material into the reactor. In embodiments that include the use of a cooling system, the cooling system includes an active cooling unit (e.g., a heat exchanger) capable of lowering the temperature of the biomass. In some embodiments, two or more of the drier, grinding system, and cooling system may be combined in a single unit. The cooling system may be, in some embodiments, directly integrated with one or more reactors.

As illustrated in FIG. 7, the feed composition may be transferred to the reactor 1-3. The reactor may be used, in some instances, to perform catalytic pyrolysis of an organic material. In the illustrative embodiment of FIG. 7, the reactor comprises any suitable reactor known to those skilled in the art. For example, in some instances, the reactor may comprise a continuously stirred tank reactor (CSTR), a batch reactor, a semi-batch reactor, or a fixed bed catalytic reactor. In some cases, the reactor comprises a fluidized bed reactor and a fixed bed reactor, e.g., a circulating fluidized bed reactor. Fluidized bed reactor may, in some cases, provide improved mixing of the catalyst and/or organic material during pyrolysis and/or subsequent reaction processes, which may enhance the control over the reaction products formed. The use of fluidized bed reactor may also improve heat transfer within the reactor. In addition, improved mixing in a fluidized bed reactor may lead to a reduction of the amount of coke adhered to the catalyst, resulting in reduced deactivation of the catalyst in some cases. As used herein, the term "fluidized bed reactor" is given its conventional meaning in the art and is used to refer to reactors comprising a vessel that can contain a granular solid material (e.g., silica particles, catalyst particles, etc.), in which a fluid (e.g., a gas or a liquid) is passed through the granular solid material at velocities sufficiently high as to suspend the solid material and cause it to behave as though it was a fluid. The term "circulating fluidized bed reactor" is also given its conventional meaning in the art and is used to refer to fluidized bed reactors in which the granular solid material is passed out of the reactor, circulated through a line in fluid communication with the reactor, and recycled back into the reactor.

Bubbling fluidized bed reactors and turbulent fluidized bed reactors are also known to those skilled in the art. In bubbling fluidized bed reactors, the fluid stream used to fluidize the granular solid material is operated at a sufficiently low flow rate such that bubbles and voids are observed within the volume of the fluidized bed during operation. In turbulent fluidized bed reactors, the flow rate of the fluidizing stream is higher than that employed in a bubbling fluidized bed reactor, and hence, bubbles and voids are not observed within the volume of the fluidized bed during operation. As used herein, the term "fixed bed reactor" is a conventionally defined reactor in the art and is also referred to as packed bed reactor, which is loaded with a solid catalyst or a solid reactant to achieve the process of a multi-phase reaction. The solid typically appears granular and has a particle size of about 2-15 mm, and are stacked to be a bed layer with a certain height (or thickness). The bed layer is static and fluid passes the bed layer to perform reaction. Its difference from fluidized bed reactor and moving bed reactor is the static state of solid granules. The trickle bed reactor may also belong to fixed bed reactors, in which gas and liquid phases co-currently downwardly pass through the bed layer, presenting a contact of gas liquid solid phases. Fixed bed reactors have three essential forms: □ axial thermal insulating fixed bed reactor, in which fluid flows through the bed layer along the axial direction from the top to the bottom, and there is no heat exchange between the bed layer and the exterior; □ radial thermal insulating fixed bed reactor, in which fluid flows through the bed layer along the radial direction, and centrifugal flow or centripetal flow may be used and there is no heat exchange between the bed layer and the exterior; □ tubular fixed bed reactor, composed of several reaction tubes in parallel. Catalyst is placed within tubes or between tubes, a heat carrier flows within tubes or between tubes to perform heating or cooling. The diameter of the tube is typically between 25-50 mm. The number of the tubes may be up to 10 thousand.

The reactor(s) may have any suitable size for performing the processes described herein. For example, the reactor may have a volume between 0.1-1 L, 1-50 L, 50-100 L, 100-250 L, 250-500 L, 500-1000 L, 1000-5000 L, 5000-10,000 L, or 10,000-50,000 L. In some instances, the reactor has a volume greater than about 1 L, or in other instances, greater than about 10 L, 50 L, 100 L, 250 L, 500 L, 1,000 L, or 10,000 L. Reactor volumes greater than 50,000 L are also possible. The reactor may be cylindrical, spherical, or any other suitable shape.

The inventors have discovered that higher yields of desired product production, lower yields of coke formation, and/or more controlled obtaining of target products (e.g., nitrogen-containing aromatic compounds) can be achieved when particular combinations of reactions conditions and system components are implemented in methods and systems described herein. As an example, reaction conditions, for example at least one of temperature of the reactor and/or solids separator, reactor pressure, heating rate of the feed stream, catalyst to organic material mass ratio, weight hourly space velocities, residence time of the organic material in the reactor, residence time of the reaction product in the solids separator, and/or catalyst type (as well as silica to alumina molar ratio for zeolite catalysts) can be controlled to achieve beneficial results, as described below.

The reactor(s) may be operated at any suitable temperature. In some instances, it may be desirable to operate the reactor at relatively high temperatures. For example, the reactor may be operated at temperatures of at least about 300° C., at least about 400° C., at least about 500° C., at least about 600° C., at least about 700° C., at least about 800° C. In some embodiments, the reactor may be operated at temperatures between about 500° C. and about 800° C., between about 525° C. and about 800° C., between about 550° C. and about 700° C., or between about 575° C. and about 650° C. The reaction under low-temperature condition is favorable to generate pyrrole and pyrazine compounds; and the reaction under high-temperature condition is vigorous and is favorable to generate pyridine, indole, and aniline compounds. In other embodiments, the reactor may be operated between about 500° C. and about 600° C. The reactor(s) may also be operated at any suitable pressure. In some embodiments, the reactor may be operated at a pressure of about 0.1-4 MPa. In some embodiments, the reactor may be operated at a pressure of at least about 1 atm, at least about 5 atm, at least about 1 MPa, or at least about 4 MPa. In some embodiments, the weight hourly space velocity of the organic material may be selected to selectively produce a desired set of fluid products. As used herein, the term "weight hourly space velocity" is defined as the mass flow rate of the organic material into the reactor (e.g., as measured in g/hr) divided by the mass of catalyst in the reactor (e.g., as measured in g) and in units of reciprocal of time. The weight hourly space velocity of the organic material in a reactor may be calculated using different methods depending upon the type of reactor used. For example, for systems employing batch or semi-batch reactors, the organic material does not have a weight hourly space velocity. For systems in which catalyst is fed to and/or extracted from the reactor during reaction (e.g., circulating fluidized bed reactors), the weight hourly space velocity may be determined by calculating the average amount of catalyst within the volume of the reactor over a period of operation (e.g., steady-state operation). Any suitable weight hourly space velocity may be used in the embodiments described herein. In some instances, a weight hourly space velocity of less than about 10 $hour^{-1}$, less than about 5 $hour^{-1}$, less than about 1 $hour^{-1}$, less than about 0.5 $hour^{-1}$, less than about 0.1 $hour^{-1}$, less than about 0.05 $hour^{-1}$, or less than about 0.01 $hour^{-1}$ may be employed. In some embodiments, a weight hourly space velocity of between about 0.01 $hour^{-1}$ and about 10 $hour^{-1}$, between about 0.01 $hour^{-1}$ and about 5 $hour^{-1}$, between about 0.01 $hour^{-1}$ and about 0.1 $hour^{-1}$, between about 0.1 $hour^{-1}$ and about 1 $hour^{-1}$, or between about 1 $hour^{-1}$ and about 10 $hour^{-1}$ may be employed. It may also be advantageous for a fluidized bed reactor, in some embodiments, to employ weight hourly space velocities of less than about 1 $hour^{-1}$, less than about 0.5 $hour^{-1}$, less than about 0.1 $hour^{-1}$, less than about 0.05 $hour^{-1}$, less than about 0.01 $hour^{-1}$, between about 0.01 $hour^{-1}$ and 0.1 $hour^{-1}$, or between about 0.1 $hour^{-1}$ and 1 $hour^{-1}$.

Some embodiments comprise varying the weight hourly space velocity of the organic material to selectively produce different fluid products. For example, in some embodiments, varying the weight hourly space velocity of the organic material can control the relative amounts of nitrogen-containing aromatic compounds and olefin compounds in the reaction products. For example, relatively low weight hourly space velocities may be used to produce a relatively larger amount of nitrogen-containing aromatic compounds than olefins. Relatively high weight hourly space velocities may be used to produce a relatively larger amount of olefins than nitrogen-containing aromatic compounds. In some embodiments, solid organic material is provided in a fluidized bed reactor at a weight hourly space velocity of between about 0.1 $hour^{-1}$ and about 10 $hour^{-1}$ to selectively produce olefin compounds, or between about 0.01 $hour^{-1}$ and about 0.1 $hour^{-1}$ to selectively produce nitrogen-containing aromatic compounds. In some instances, it is beneficial to control the residence time of the organic material (e.g., a solid organic material) in the reactor and/or under a defined set of reaction conditions (i.e. conditions under which the organic material can undergo pyrolysis in a given reactor system). In continuous flow systems, the residence time of the organic material in the reactor is defined as the amount of time the organic material and any reaction products formed therefrom (excluding products that accumulate in the reactor such as, for example, coke deposited on the catalyst) spend in the reactor. The residence time of the organic material in a reactor may be calculated using different methods depending upon the type of reactor used. For example, in embodiments in which the reactor comprises a packed bed reactor into which only organic material is continuously fed (i.e. no carrier or fluidizing flow is utilized), the residence time of the organic material in the reactor as used herein can be determined by the volume of the reactor divided by the volumetric flow rate of the product gases exiting the reactor. In cases where the reaction takes place in a reactor that is closed to the mass flow during operation (e.g., a batch reactor), the residence time of the organic material in such a reactor is defined as the amount of time elapsing between the time at which the temperature in the reactor containing the organic material reaches a level sufficient to commence a pyrolysis reaction (e.g. typically about 300° C. to about 800° C. for many typical organic feed stock materials) and the time at which the reactor is quenched (e.g., cooled to a temperature below that sufficient to support further pyrolysis, e.g., typically about 300° C. to about 800° C. for many typical organic feed stock materials).

In some cases, e.g. for certain fluidized bed reactors, the feed stream may include fluidization fluid. In cases where circulating fluidized beds are used, catalyst and fluidization fluid may both be fed/recycled to the reactor. In some cases, the auxiliary materials may comprise contaminants entrained in the organic material. In such cases, the residence time of the organic material in the reactor can be determined as the volume of the reactor divided by the volumetric flow rates of the organic material and reaction product gases exiting the reactor as with the packed bed situation described above; however, since the flow rates of the organic material and reaction product gases exiting the reactor may not be convenient to determine directly, the volumetric flow rates of the organic material and reaction product gases exiting the reactor may be estimated by subtracting the feed volumetric flow rate of the auxiliary materials (e.g., fluidization fluid, catalyst, contaminants, etc.) into the reactor from the total volumetric flow rate of the gas stream exiting the reactor. In some embodiments, the residence time of a material (e.g., an organic material or any other suitable feed material) in the reactor is at least about 2 seconds, at least about 5 seconds, at least about 10 seconds, at least about 30 seconds, at least about 60 seconds, at least about 120 seconds, at least about 240 seconds, or at least about 480 seconds. In some cases, the residence time of a material (e.g., an organic material or any other suitable feed material) in the reactor is less than about 5 minutes, between about 1 minute and about 4 minutes, or from about 2 seconds to about 480 seconds. Previous "fast pyrolysis" studies have, in many cases, employed systems with very short feed material (e.g., organic material) residence times (e.g., less than 2 seconds). The inventors have discovered, however, that in some cases, the use of relatively longer residence times allows adequate time for additional chemical reactions to form desirable products. Long residence times can be achieved by, for example, increasing the volume of the reactor and/or reducing the volumetric flow rate of the organic material. It should be understood, however, that in some embodiments described herein, the residence time of the feed material (e.g., organic material) may be relatively shorter, e.g., less than about 2 seconds or less than about 1 second.

In certain cases where fluidized bed reactors are used, the feed material (e.g., a solid organic material) in the reactor may be fluidized by flowing a fluid through the reactor. In the exemplary embodiment of FIG. 7, a fluid stream 2-8 is used to fluidize the feed material in reactor 1-3. Fluid may be supplied to the fluid stream from a fluid source 1-10 and/or from the product stream of the reactor via a compressor 1-9 (which will be described in more detail below). As used herein, the term "fluid" means a material generally in a liquid, supercritical, or gaseous state. Fluids, however, may also contain solids such as, for example, suspended or colloidal particles. In some embodiments, it may be advantageous to control the residence time of the fluidization fluid in the reactor. The residence time of the fluidization fluid is defined as the volume of the reactor divided by the volumetric flow rate of the fluidization fluid. In some cases, the residence time of the fluidization fluid may be at least about 5 seconds, at least about 10 seconds, at least about 30 seconds, at least about 60 seconds, at least about 120 seconds, at least about 240 seconds, or at least about 480 seconds. In some cases, the residence time of the fluidization fluid may be from about 2 seconds to about 480 seconds, from about 5 seconds to about 480 seconds, from about 10 seconds to about 480 seconds, from about 30 seconds to about 480 seconds, from about 60 seconds to about 480 seconds, from about 120 seconds to about 480 seconds, or from about 240 seconds to about 480 seconds.

Suitable fluidization fluids that may be used in this invention include, for example, inert gases (such as helium gas, argon gas, neon gas, nitrogen gas, etc.) and ammonia gas.

As shown in the illustrative embodiment of FIG. 7, the products (e.g., fluid products) formed during the reaction of the organic material exit the reactor via a product stream 2-3. In addition to the reaction products, the product stream may, in some cases, comprise unreacted organic material, fluidization fluid, and/or catalyst. In one set of embodiments, the desired reaction products (e.g., liquid nitrogen-containing aromatic compounds, olefins, gaseous products, etc.) may be recovered from an effluent stream of the reactor. In some embodiments, optional product reactor 1-4 can be incorporated into the process. The product reactor can be used, for example, to convert one or more of the fluid products (e.g., olefins, nitrogen-containing aromatic compounds, etc.) in product stream 2-3 to one or more other products. In some cases, the product reactor may contain a catalyst (e.g., a zeolite catalyst) which can be used to perform one or more catalytic reactions. One of ordinary skill in the art is capable of selecting appropriate reactor types and/or conditions for performing such reactions.

As shown in the illustrative embodiment of FIG. 7, product stream 2-3 may be fed to an optional solids separator 1-5. The solids separator may be used, in some cases, to separate the reaction products from catalyst (e.g., at least partially deactivated catalyst) present in the product stream. In addition, the solids separator may be used, in some instances, to remove coke and/or ash from the catalyst. In some embodiments, the solids separator may comprise an optional purge stream 2-10, which may be used to purge coke, ash, and/or catalyst from the solids separator. The equipment required achieving the solids separation and/or decoking steps can be readily designed by one of ordinary skill in the art. For example, in one set of the embodiments, the solids separator may comprise a vessel comprising a mesh material that defines a retaining portion and a permeate portion of the vessel. The mesh may serve to retain the catalyst within the retaining portion while allowing the reaction product to pass to the permeate portion. The catalyst may exit the solids separator through a port on the retaining side of the mesh while the reaction product may exit a port on the permeate side of the mesh. The solids separator may be operated at any suitable temperature. In some embodiments, the solids separator may be operated at elevated temperatures. The inventors have discovered that for certain reactions, the use of elevated temperatures in the solids separator can allow for additional reforming and/or reaction of the compounds from the reactor. This may allow for the increased formation of desirable products. Not wishing to be bound by any theory, elevated temperatures in the solids separator may provide enough energy to drive endothermic reforming reactions. The solids separator may be operated at a temperature of, for example, between about 25° C. and about 200° C., between about 200° C. and about 500° C., between about 500° C. and about 600° C., or between about 600° C. and about 800° C. In some cases, the solids separator may be operated at temperatures of at least about 500° C., at least about 600° C., at least 700° C., at least 800° C., or higher. In some cases, it may be beneficial to control the residence time of the catalyst in the solids separator. The residence time of the catalyst in the solids separator is defined as the volume of the solids separator divided by the volumetric flow rate of the catalyst through the solids separator. In some cases, relatively long residence times of the catalyst in the solids separator may be desired in order to facilitate the removal of sufficient amounts of ash, coke, and/or other undesirable products from the catalyst. In addition, the inventors have discovered that by employing relatively long residence times of the catalyst in the solids separator, the pyrolysis products may be further reacted to produce desirable products. In some embodiments, the residence time and temperature in the solids separator are together selected such that a desired product stream is produced. In some embodiments, the residence time of the catalyst in the solids separator is at least about 1 second, at least about 5 seconds, at least about 10 seconds, at least about 30 seconds, at least about 60 seconds, at least about 120 seconds, at least about 240 seconds, at least about 300 seconds, at least about 600 seconds, or at least about 1200 seconds. Methods for controlling the residence time of the catalyst in the solids separator are known by those skilled in the art. For example, in some cases, the interior wall of the solids separator may comprise baffles that serve to restrict the flow of catalyst through the solids separator and/or increase the path length of fluid flow in the solids separator. Additionally, the residence time of the catalyst in the solids separator may be controlled by controlling the flow rate of the catalyst through the solids separator (e.g., by controlling the flow rate of the fluidizing fluid through the reactor). The solids separator may have any suitable size. For example, the solids separator may have a volume between 0.1-1 L, 1-50 L, 50-100 L, 100-250 L, 250-500 L, 500-1000 L, 1000-5000 L, 5000-10,000 L, or 10,000-50,000 L. In some instances, the solids separator has a volume greater than about 1 L, or in other instances, greater than about 10 L, 50 L, 100 L, 250 L, 500 L, 1,000 L, or 10,000 L. Solids separator volumes greater than 50,000 L are also possible. The solids separator may be cylindrical, spherical, or any other shape and may be circulating or non-circulating. In some embodiments, the solids separator may comprise a vessel or other unit operation similar to that used for one or more of the reactor(s) used in the process. The flow of the catalyst in the solids separator may comprise any suitable geometry. For example, the flow path may be substantially straight. In some cases, the solids separator may comprise a flow channel with a serpentine, meandering, helical, or any other suitable shape. The ratio of the length of the flow path of the solids separator (or, in certain embodiments, the path length of the catalyst through the solids separator) to the average diameter of the solids separator channel may comprise any suitable ratio. In some cases, the ratio may be at least 2:1, at least 5:1, at least 10:1, at least 50:1, at least 100:1, or greater. The parameters outlined above may be used in any suitable combination to produce desirable reaction products (e.g., nitrogen-containing aromatic compounds) and/or favorable yields or particular components. For example, the use of long residence times may be combined with the use of a circulating or turbulent fluidized bed reactor to process solid organic material. In some embodiments, relatively high temperatures (e.g., at least 500° C.) and long residence times (e.g., at least about 1 second, at least about 5 seconds, at least about 10 seconds, at least about 30 seconds, at least about 60 seconds, at least about 120 seconds, at least about 240 seconds, at least about 300 seconds, at least about 600 seconds, or at least about 1200 seconds, etc.) may be used in the solids separator after pyrolyzing a solid organic material in the reactor. In other embodiments, relatively low weight hourly space velocities (e.g., less than about 0.1 $hour^{-1}$, less than about 0.05 $hour^{-1}$, less than about 0.01 $hour^{-1}$, etc.) may be used in a fluidized bed reactor to produce a relatively larger amount of nitrogen-containing aromatic compounds than olefins, e.g., at least about 6% nitrogen-containing aromatic compounds or more. In another set of embodiments, a solid organic material and a zeolite catalyst comprising a large silica to alumina molar ratio (e.g., at least about 15) may be heated in a reactor at a high rate. In some cases, a catalyst and a solid organic material may be fed to a reactor in a mass ratio of at least about 0.5:1 and heated to a temperature of, for example, between 500° C. and 800° C. In some instances, a catalyst and a solid organic material may be fed to a reactor in a mass ratio of at least about 0.5:1 such that the mixture has a relatively long residence time (e.g., at least about 5 seconds). In yet another set of embodiments, a relatively high fluidization fluid residence time (e.g., at least about 5 seconds) and a relatively high reactor temperature (e.g., between about 500° C. and about 800° C.) may be used.

As previously mentioned, the solids separator may not be required in all embodiments. For example, for situations in which catalytic fixed bed reactors are employed, the catalyst may be retained within the reactor, and the reaction products may exit the reactor substantially free of catalyst, thus negating the need for a separate separation step.

In the set of embodiments illustrated in FIG. 7, separated catalyst may exit the solids separator via stream 2-4. In some cases, the catalyst exiting the separator may be at least partially deactivated. The separated catalyst may be fed, in some embodiments, to a catalyst regenerator 1-8 in which any catalyst that was at least partially deactivated may be re-activated. In some embodiments, the catalyst regenerator may comprise optional purge stream 2-11, which may be used to purge coke, ash, and/or catalyst from the regenerator. Methods for activating catalyst are well-known to those skilled in the art. In one set of embodiments, an oxidizing agent is fed to the catalyst regenerator via a stream 2-6, e.g., as shown in FIG. 7. The oxidizing agent may originate from any source including, for example, a tank of oxygen, atmospheric air, steam, among others. In the regenerator, the catalyst is re-activated by reacting the catalyst with the oxidizing agent. In some cases, the deactivated catalyst may comprise residual carbon and/or coke, which may be removed via reaction with the oxidizing agent in the regenerator. The regenerator in FIG. 7 comprises a vent stream 2-12 which may include regeneration reaction products, residual oxidizing agent, etc. The catalyst regenerator may be of any suitable size mentioned above in connection with the reactor or the solids separator. In addition, the regenerator may be operated at elevated temperatures in some cases (e.g., at least about 300° C., 400° C., 500° C., 600° C., 700° C., 800° C., or higher). The residence time of the catalyst in the regenerator may also be controlled using methods known by those skilled in the art, including those outlined above. In some instances, the mass flow rate of the catalyst through the regenerator will be coupled to the flow rate(s) in the reactor and/or solids separator in order to preserve the mass balance in the system. As shown in the illustrative embodiment of FIG. 7, the regenerated catalyst may exit the regenerator via stream 2-7. The regenerated catalyst may be recycled back to the reactor via recycle stream 2-8. In some cases, catalyst may be lost from the system during operation. In some such and other cases, additional catalyst may be added to the system via a makeup stream 2-12. As shown illustratively in FIG. 7, the regenerated and makeup catalyst may be fed to the reactor together with the fluidization fluid via recycle stream 2-8, although in other embodiments, the catalyst and fluidization fluid may be fed to the reactor via separate streams. Referring back to solids separator 1-5 in FIG. 7, the reaction products (e.g., fluid nitrogen-containing aromatic products) exit the solids separator via stream 2-3. In some cases, the reaction products in stream 2-7 may be fed to an optional condenser 1-6. The condenser may comprise a heat exchanger which condenses at least a portion of the reaction product from a gaseous to a liquid state. The condenser may be used to separate the reaction products into gaseous, liquid, and solid components. The operation of condensers is well known to those skilled in the art.

The condenser may also, in some embodiments, make use of pressure change to condense portions of the product stream. In FIG. 7, stream 2-13 may comprise the liquid components of the reaction products (e.g., water, nitrogen-containing aromatic compounds, olefin compounds, etc.), and stream 2-14 may comprise the gaseous components of the reaction products (e.g., CO, $CO_2$, $H_2$, $NH_3$, etc). In some embodiments, the gaseous components may be fed to a vapor recovery system 1-7. The vapor recovery system may be used, for example, to recover any desirable vapors in stream 2-14 and transport them via stream 2-15. In addition, stream 2-16 may be used to transport CO, $CO_2$, and/or other non-recoverable gases from the vapor recovery system. It should be noted that, in some embodiments, the optional vapor recovery system may be placed in other locations. For example, in some embodiments, a vapor recovery system may be positioned downstream of purge stream 2-13. One skilled in the art can select an appropriate placement for a vapor recovery system. Other products (e.g., excess gas) may be transported to optional compressor 1-9 via stream 2-17, where they may be compressed and used as fluidization gas in the reactor and/or where they may assist in transporting the organic material to the reactor. In some instances, the liquid components may be further processed, for example, to separate the water phase from the organic phase, to separate individual compounds, etc. It should be understood that, while the set of embodiments illustrated by FIG. 7 include a reactor, solids separator, regenerator, condenser, etc., not all embodiments will involve the use of these elements. For example, in some embodiments, the feed stream may be fed to a catalytic fixed bed reactor, reacted, and the reaction products may be collected directly from the reactor and cooled without the use of a dedicated condenser. In some instances, while a dryer, grinding system, solids separator, regenerator, condenser, and/or compressor may be used as part of the process, one or more of these elements may comprise separate units not fluidically and/or integrally connected to the reactor. In other embodiments one or more of the dryer, grinding system, solids separator, regenerator, condenser, and/or compressor may be absent. In some embodiments, the desired reaction product (e.g., nitrogen-containing aromatic compounds, olefins, gaseous products, etc.) may be recovered at any point in the production process (e.g., after passage through the reactor, after separation, after condensation, etc.).

In some embodiments, a process of the invention may involve the use of more than one reactor. For example, multiple reactors may be connected in fluid communication with each other. In some embodiments, the process may comprise providing an organic material in a first reactor and pyrolyzing, within the first reactor, at least a portion of the organic material under reaction conditions sufficient to produce one or more pyrolysis products. In some embodiments, a catalyst may be provided to the first reactor, and at least a portion of the one or more pyrolysis products in the first reactor are catalytically reacted using the catalyst under reaction conditions sufficient to produce one or more fluid products. The process may further comprise catalytically reacting at least a portion of the one or more pyrolysis products in a second reactor using a catalyst under reaction conditions sufficient to produce one or more fluid products. In some cases, after catalytically reacting at least a portion of the one or more pyrolysis products in the second reactor, the process may comprise a step of further reacting within the second reactor at least a portion of the one or more fluid products from the first reactor to produce one or more other products. One or more of the reactors in a multiple reactor configuration may comprise a fluidized bed reactor (e.g., a circulating fluidized bed reactor, a turbulent fluidized bed reactor, etc.) and a fixed bed reactor (such as an axial thermal insulating fixed bed reactor, a radial thermal insulating fixed bed reactor, a tubular fixed bed reactor, etc) or, in other instances, any other type of reactor (e.g., any of the reactors mentioned above). For example, in one set of embodiments, the first reactor comprises a circulating fluidized bed reactor or a turbulent fluidized bed reactor, and the second reactor comprises a circulating fluidized bed reactor or a turbulent fluidized bed reactor in fluid communication with the first reactor. In addition, the multiple reactor configuration may include any of the additional processing steps and/or equipment mentioned herein (e.g., a solids separator, a regenerator, a condenser, etc.). The reactors and/or additional processing equipment may be operated using any of the processing parameters (e.g., temperatures, residence times, etc.) mentioned herein.

Organic materials useful in this invention may include, for example, a component such as xylitol, xylose, xylan, glucose, cellobiose, cellulose, starch, hemicellulose, chitosan, chitin, sucrose, fructose, wood, bagasse, bamboo, corn straws, waste paper, rapeseed meal, Jatropha curcas meal, soybean meal, lee, waste proteins, microalgae, etc., and the pyrolysis products thereof, and combinations of such components and/or the pyrolysis products thereof. Other examples of organic materials include, for example, plastic waste, recycled plastics, agricultural and municipal solid waste, food waste, animal waste, carbohydrates, lignocellulosic materials (e.g., wood chips or shavings, lignocellulosic biomass, etc.), or combinations thereof, among others. The organic materials further include liquid materials, such as aqueous glucose solution, furan, methylfuran, 2,5-dimethylfuran, furfural, 5-hydroxymethylfurfural, 5-methylfurfural, γ-valerolactone, cellulose bio-oils, water-soluble bio-oils, water-insoluble bio-oils, and the like, or a combination thereof. Bio-oils (normal bio-oils) are mainly derived from concentrated liquid of oxygen-containing hydrocarbon compounds generated by pyrolysis of biomass raw materials. For example, biomass is pyrolyzed under an anoxic or hypoxic condition at a suitable temperature (450-650° C.) to generate pyrolysis gases, which are then condensed to obtain bio-oils. Bio-oils are complex mixtures, in which water, furan compounds, organic acids such as acetic acid, formic acid, etc, and aromatic compounds such as guaiacol, eugenol, phenol, catechol, vanillin, etc are contained. Biomass mainly comprises the raw materials described above. Water-soluble bio-oils are mainly derived from water separated products of bio-oils: bio-oils and water are formulated into a mixture at a certain ratio, and then the mixture is centrifuged in a centrifuge at a certain rotational speed for a period of time to allow layer separation. The upper layer, which is water-soluble bio-oils, is decanted, and the remaining part is water-insoluble bio-oils.

As illustrated herein, the choice of organic materials and catalyst materials can be used to vary the composition of the resulting fluid products. As described above, the organic material in the feed composition may comprise a solid, liquid, and/or gas. In cases where the organic material includes solids, the solids may be of any suitable size. In some cases, it may be advantageous to use organic material solids with relatively small particle sizes. Small-particle solids may, in some instances, react more quickly than larger solids, due to their relatively higher surface area to volume ratios compared to larger solids. In addition, small particle sizes may allow for more efficient heat transfer within each particle and/or within the reactor volume. This may prevent or reduce the formation of undesired reaction products. Moreover, small particle sizes may increase solid-gas and solid-solid contact, and thereby improves heat and mass transfer. In some embodiments, the average size of the solid organic material is less than about 5 mm, less than about 2 mm, less than about 1 mm, less than about 500 micrometers, less than about 60 mesh (250 micrometers), less than about 100 mesh (149 micrometers), less than about 140 mesh (105 micrometers), less than about 170 mesh (88 micrometers), less than about 200 mesh (74 micrometers), less than about 270 mesh (53 micrometers), or less than about 400 mesh (37 micrometers), or smaller. In some cases, it may be desirable to employ feed material with an average particle size above a minimum amount in order to reduce the pressure required to pass the organic material feed through the reactor. For example, in some cases, it may be desirable to use solid organic material with an average particle size of at least about 400 mesh (37 micrometers), at least about 270 mesh (53 micrometers), at least about 200 mesh (74 micrometers), at least about 170 mesh (88 micrometers), at least about 140 mesh (105 micrometers), at least about 100 mesh (149 micrometers), at least about 60 mesh (250 micrometers), at least about 500 micrometers, a least about 1 mm, at least about 2 mm, at least about 5 mm, or higher.

Catalyst components useful in this invention can be selected from any catalyst known in the art, or as would be understood by those skilled in the art made aware of this invention. Functionally, catalysts may be limited only by the capability of any of such materials to promote and/or affect dehydration, dehydrogenation, amination, isomerization, hydrogen transfer, aromatization, decarbonylation, decarboxylation, aldol condensation and/or any other reaction related to the pyrolysis of organic materials. Catalyst components can be considered acidic, neutral or basic, as would be understood by those skilled in the art.

The catalyst particles described herein can comprise polycrystalline solids (e.g., polycrystalline particles) in some cases. In some embodiments, the catalyst particles can also comprise single crystals. In certain cases, the particles may be distinct and separate physical objects that are stand-alone.

In other cases, the particles may, at least at certain points in their preparation and/or use, comprise an agglomerate of a plurality of individual particles in intimate contact with each other.

A catalyst used in embodiments described herein (e.g., in the feed stream, in the reactor, etc.) may be of any suitable size. In some cases, it may be advantageous to use a catalyst of smaller particles. As mentioned previously, in certain embodiments, the catalyst particles may be in the object form of larger catalyst particles that may be comprised of a plurality of agglomerated catalyst particles. In some embodiments, for example, the use of small catalyst particles may increase the extent to which the organic material may contact the surface sites of the catalyst due to increased external catalytic surface area and decreased diffusion distances through the catalyst. In some cases, catalyst size and/or catalyst particle size may be chosen at least in part based on, for example, the type of fluid flow desired and the catalyst lifetime.

In some embodiments, the average diameter (as measured by conventional sieve analysis) of catalyst objects, which may in certain instances comprise a single catalyst particle or in other instances comprise an agglomerate of a plurality of particles, may be less than about 5 mm, less than about 2 mm, less than about 1 mm, less than about 500 micrometers, less than about 60 mesh (250 micrometers), less than about 100 mesh (149 micrometers), less than about 140 mesh (105 micrometers), less than about 170 mesh (88 micrometers), less than about 200 mesh (74 micrometers), less than about 270 mesh (53 micrometers), or less than about 400 mesh (37 micrometers), or smaller.

In some embodiments, the catalyst objects can be or be formed of particles having a largest cross-sectional dimension of less than about 5 micrometers, less than about 1 micrometer, less than about 500 nm, less than about 100 nm, between about 100 nm and about 5 micrometers, between about 500 nm and about 5 micrometers, between about 100 nm and about 1 micrometer, or between about 500 nm and about 1 micrometer. As described previously, in certain cases, catalyst particles having the dimensions within the ranges described previously may be agglomerated to form separable catalyst objects having dimensions within the ranges described in the previous paragraph. As used herein, the "largest cross-sectional dimension" of a particle refers to the largest dimension between two boundaries of a particle. One of ordinary skill in the art would be capable of measuring the largest cross-sectional dimension of a particle by, for example, analyzing a scanning electron micrograph (SEM) of a catalyst preparation. In embodiments of agglomerated particles, the particles should be considered separately when determining the largest cross-sectional dimensions. In such a case, the measurement would be performed by establishing imaginary boundaries between each of the agglomerated particles, and measuring the largest cross-sectional dimension of the hypothetical, individuated particles that result from such boundaries. In some embodiments, a relatively large number of the particles within a catalyst have largest cross-sectional dimensions that lie within a given range. For example, in some embodiments, at least about 50%, at least about 75%, at least about 90%, at least about 95%, or at least about 99% of the particles within a catalyst have largest cross-sectional dimensions of less than about 5 micrometers, less than about 1 micrometer, less than about 500 nm, less than about 100 nm, between about 100 nm and about 5 micrometers, between about 500 nm and about 5 micrometers, between about 100 nm and about 1 micrometer, or between about 500 nm and about 1 micrometer.

A relatively large proportion of the volume of the catalyst can be occupied by particles with largest cross-sectional dimensions within a specific range, in some cases. For example, in some embodiments, at least about 50%, at least about 75%, at least about 90%, at least about 95%, or at least about 99% of the sum of the volumes of all the catalyst used is occupied by particles having largest cross-sectional dimensions of less than about 5 micrometers, less than about 1 micrometer, less than about 500 nm, less than about 100 nm, between about 100 nm and about 5 micrometers, between about 500 nm and about 5 micrometers, between about 100 nm and about 1 micrometer, or between about 500 nm and about 1 micrometer.

In some embodiments, the particles within a catalyst substantially have the same size. For example, the catalyst can comprise particles with a distribution of dimensions such that the standard deviation of the largest cross-sectional dimensions of the particles is no more than about 50%, no more than about 25%, no more than about 10%, no more than about 5%, no more than about 2%, or no more than about 1% of the average largest cross-sectional dimensions of the particles. Standard deviation ($\sigma$) is given its normal meaning in the art, and may be calculated as:

$$\sigma = \sqrt{\frac{\sum_{i=1}^{n} (D_i - D_{avg})^2}{n-1}}$$

wherein Di is the largest cross-sectional dimension of particle i, Davg is the average of the largest cross-sectional dimensions of all the particles, and n is the number of particles within the catalyst. The percentage comparison between the standard deviation described above and the average largest cross-sectional dimension of the particles can be obtained by dividing the standard deviation by the average and multiplying by 100%. The use of a catalyst including particles within a chosen size distribution indicated above can lead to an increase in the yield and/or selectivity of nitrogen-containing aromatic compounds produced by the reaction of the organic material. For example, in some cases, the use of a catalyst containing particles with a desired size range (e.g., any of the size distributions outlined above) can result in an increase in the amount of nitrogen-containing aromatic compounds in the reaction products of at least about 5%, at least about 10%, or at least about 20%, relative to an amount of nitrogen-containing aromatic compounds that would be produced using a catalyst containing particles with a size distribution outside the desired range (e.g., with a large percentage of particles larger than 1 micrometer, larger than 5 micrometers, etc.).

Optionally, alone or in conjunction with the considerations mentioned above, catalysts can be selected according to pore size (e.g., mesoporous type and pore sizes typically associated with zeolites), e.g., average pore sizes of less than about 100 Angstroms, less than about 50 Angstroms, less than about 20 Angstroms, less than about 10 Angstroms, less than about 5 Angstroms, or smaller. In some embodiments, catalysts with average pore sizes of from about 5 Angstroms to about 100 Angstroms may be used. In some embodiments, catalysts with average pore sizes of between about 5.5 Angstroms and about 6.5 Angstroms, or between about 5.9 Angstroms and about 6.3 Angstroms may be used. In some cases, catalysts with average pore sizes of between about 7 Angstroms and about 8 Angstroms, or between about 7.2 Angstroms and about 7.8 Angstroms may be used. As used herein, the term "pore size" is used to refer to the smallest cross-sectional diameter of a pore. The smallest cross-sectional diameter of a pore may correspond to the smallest cross-sectional dimension (e.g., a cross-sectional diameter) as measured perpendicularly to the length of the pore. In some embodiments, a catalyst with an "average pore size" or a "pore size distribution" of X refers to a catalyst in which the average of the smallest cross-sectional diameters of the pores within the catalyst is about X. It should be understood that "pore size" or "smallest cross sectional diameter" of a pore as used herein refers to the Norman radii adjusted pore size well known to those skilled in the art.

One of ordinary skill in the art will understand how to determine the pore size (e.g., minimum pore size, average of minimum pore sizes) in a catalyst. For example, XRD may be used for determining pore sizes (e.g., zeolite pore sizes), and other techniques include, for example, helium pycnometry or low pressure argon adsorption technique. Unless otherwise indicated, pore sizes referred to herein are those determined by x-ray diffraction corrected as described above to reflect their Norman radii adjusted pore sizes.

In some embodiments, a screening method is used to select catalysts with appropriate pore sizes for the conversion of specific pyrolysis product molecules. The screening method may comprise determining the size of pyrolysis product molecules to be catalytically reacted (e.g., the molecule kinetic diameters of the pyrolysis product molecules). One of ordinary skill in the art can calculate, for example, the kinetic diameter of a given molecule. The type of catalyst may then be chosen such that the pores of the catalyst (e.g., Norman adjusted minimum radii) are sufficiently large to allow the pyrolysis product molecules to diffuse into and/or react with the catalyst. In some embodiments, the catalysts may be chosen such that their pore sizes are sufficiently small to prevent entry and/or reaction of other pyrolysis products whose reactions are undesirable.

Without limitation, some such and other catalysts can be selected from naturally-occurring zeolites, synthetic zeolites and combinations thereof. In certain embodiments, the catalyst may be a Mordenite Framework Inverted (MFI) type zeolite catalyst, such as a ZSM-5 zeolite catalyst, as would be understood by those skilled in the art. Optionally, such a catalyst can comprise acidic sites. Other types of zeolite catalysts include ferrierite, zeolite Y, zeolite beta, modernite, MCM-22, ZSM-23, ZSM-57, SUZ-4, EU-1, ZSM-11, (S) AlPO-31, SSZ-23, among others. In other embodiments, non-zeolite catalysts, for example, $WO_x/ZrO_2$, aluminum sulfate, etc., may be used.

In some embodiments, the catalyst may comprise a metal and/or a metal oxide. Suitable metals and/or oxides include, for example, nickel, platinum, vanadium, palladium, manganese, cobalt, zinc, copper, chromium, gallium, and/or any oxide thereof, among others. In some embodiments, the metal and/or metal oxide can be impregnated into the catalyst (e.g., in the interstices of the lattice structure of the catalyst). The metal and/or metal oxide might be incorporated into the lattice structure of the catalyst. For example, the metal and/or metal oxide might be included during the preparation of the catalyst, and the metal and/or metal oxide can occupy a lattice site of the resulting catalyst (e.g., a zeolite catalyst). As another example, the metal and/or metal oxide can react or otherwise interact with a zeolite such that the metal and/or metal oxide displaces an atom within the lattice structure of the zeolite.

In certain embodiments, a Mordenite Framework Inverted (MFI) zeolite catalyst comprising gallium can be used. For example, a galloaluminosilicate MFI (GaAlMFI) zeolite catalyst can be used. One of ordinary skill in the art would be familiar with GaAlMFI zeolites, which can be thought of as aluminosilicate MFI zeolites in which some of the Al atoms have been replaced with Ga atoms. In some instances, the zeolite catalyst can be in the hydrogen form (e.g., H—GaAlMFI). In some embodiments, the galloaluminosilicate MFI catalyst can be a ZSM-5 zeolite catalyst in which some of the aluminum atoms have been replaced with gallium atoms.

In some instances, the ratio of moles of Si in the galloaluminosilicate zeolite catalyst to the sum of the moles of Ga and Al (i.e., the molar ratio expressed as Si:(Ga+Al)) in the galloaluminosilicate zeolite catalyst can be at least about 15:1, at least about 20:1, at least about 25:1, at least about 35:1, at least about 50:1, at least about 75:1, or higher. In some embodiments, it may be advantageous to employ a catalyst with a ratio of moles of Si in the zeolite to the sum of the moles of Ga and Al of between about 15:1 and about 100:1, from about 15:1 to about 75:1, between about 25:1 and about 80:1, or between about 50:1 and about 75:1. In some instances, the ratio of moles of Si in the galloaluminosilicate zeolite catalyst to the moles of Ga in the galloaluminosilicate zeolite catalyst can be at least about 15:1, at least about 60:1, at least about 120:1, at least about 200:1, between about 30:1 and about 300:1, between about 15:1 and about 200:1, between about 15:1 and about 120:1, or between about 15:1 and about 75:1. The ratio of the moles of Si in the galloaluminosilicate zeolite catalyst to the moles of Al in the galloaluminosilicate zeolite catalyst can be at least about 10:1, at least about 20:1, at least about 30:1, at least about 40:1, at least about 50:1, at least about 75:1, between about 10:1 and about 100:1, between about 10:1 and about 75:1, between about 10:1 and about 50:1, between about 10:1 and about 40:1, or between about 10:1 and about 30:1.

In addition, in some cases, properties of the catalysts (e.g., pore structure, type and/or number of acid sites, etc.) may be chosen to selectively produce a desired product. It may be desirable, in some embodiments, to employ one or more catalysts to establish a bimodal distribution of pore sizes. In some cases, a single catalyst with a bimodal distribution of pore sizes may be used (e.g., a single catalyst that contains predominantly 5.9-6.3 Angstrom pores and 7-8 Angstrom pores). In other cases, a mixture of two or more catalysts may be employed to establish the bimodal distribution (e.g., a mixture of two catalysts, each catalyst type including a distinct range of average pore sizes). In some embodiments, one of the one or more catalysts comprises a zeolite catalyst and another of the one or more catalysts comprises a non-zeolite catalyst (e.g., a mesoporous catalyst, a metal oxide catalyst, etc.).

For example, in some embodiments, at least about 70%, at least about 80%, at least about 90%, at least about 95%, at least about 98%, or at least about 99% of the pores of the one or more catalysts (e.g., a zeolite catalyst, a mesoporous catalyst, etc.) have smallest cross-sectional diameters that lie within a first size distribution or a second size distribution. In some cases, at least about 2%, at least about 5%, or at least about 10% of the pores of the one or more catalysts have smallest cross-sectional diameters that lie within the first size distribution; and at least about 2%, at least about 5%, or at least about 10% of the pores of the one or more catalysts have smallest cross-sectional diameters that lie within the second size distribution. In some cases, the first and second size distributions are selected from the ranges provided above. In certain embodiments, the first and second size distributions are different from each other and do not overlap. An example of a non-overlapping range is 5.9-6.3 Angstroms and 6.9-8.0 Angstroms, and an example of an overlapping range is 5.9-6.3 Angstroms and 6.1-6.5 Angstroms. The first and second size distributions may be selected such that the ranges are not immediately adjacent one another, an example being pore sizes of 5.9-6.3 Angstroms and 6.9-8.0 Angstroms. An example of a range that is immediately adjacent one another is pore sizes of 5.9-6.3 Angstroms and 6.3-6.7 Angstroms. As a specific example, in some embodiments, one or more catalysts are used to provide a bimodal pore size distribution for the simultaneous production of nitrogen-containing aromatic compounds and olefin compounds. That is, one pore size distribution may advantageously produce a relatively high amount of nitrogen-containing aromatic compounds, and the other pore size distribution may advantageously produce a relatively high amount of olefin compounds. In some embodiments, at least about 70%, at least about 80%, at least about 90%, at least about 95%, at least about 98%, or at least about 99% of the pores of the one or more catalysts have smallest cross-sectional diameters between about 5.9 Angstroms and about 6.3 Angstroms or between about 7 Angstroms and about 8 Angstroms. In addition, at least about 2%, at least about 5%, or at least about 10% of the pores of the one or more catalysts have smallest cross-sectional diameters between about 5.9 Angstroms and about 6.3 Angstroms; and at least about 2%, at least about 5%, or at least about 10% of the pores of the one or more catalysts have smallest cross-sectional diameters between about 7 Angstroms and about 8 Angstroms.

In some embodiments, at least about 70%, at least about 80%, at least about 90%, at least about 95%, at least about 98%, or at least about 99% of the pores of the one or more catalysts have smallest cross-sectional diameters between about 5.9 Angstroms and about 6.3 Angstroms or between about 7 Angstroms and about 200 Angstroms. In addition, at least about 2%, at least about 5%, or at least about 10% of the pores of the one or more catalysts have smallest cross-sectional diameters between about 5.9 Angstroms and about 6.3 Angstroms; and at least about 2%, at least about 5%, or at least about 10% of the pores of the one or more catalysts have smallest cross-sectional diameters between about 7 Angstroms and about 200 Angstroms. In some embodiments, at least about 70%, at least about 80%, at least about 90%, at least about 95%, at least about 98%, or at least about 99% of the pores of the one or more catalysts have smallest cross-sectional diameters that lie within a first distribution and a second distribution, wherein the first distribution is between about 5.9 Angstroms and about 6.3 Angstroms and the second distribution is different from and does not overlap with the first distribution. In some embodiments, the second pore size distribution may be between about 7 Angstroms and about 200 Angstroms, between about 7 Angstroms and about 100 Angstroms, between about 7 Angstroms and about 50 Angstroms, or between about 100 Angstroms and about 200 Angstroms. In some embodiments, the second catalyst may be mesoporous (e.g., have a pore size distribution of between about 2 nm and about 50 nm).

In some embodiments, the bimodal distribution of pore sizes may be beneficial in reaction of two or more feeds of organic material components. For example, some embodiments comprise providing a solid organic material comprising a first component and a second component in a reactor, wherein the first and second components are different. Examples of compounds that may be used as first or second components include any of the organic materials described herein (e.g., bagasse, glucose, wood, bamboo, corn straws, cellulose, hemicellulose, lignin, or any other organic material). For example, the first component may comprise one of cellulose, hemicellulose and lignin, and the second component comprises one of cellulose, hemicellulose and lignin. The method may further comprise providing first and second catalysts in the reactor. In some embodiments, the first catalyst may have a first pore size distribution and the second catalyst may have a second pore size distribution, wherein the first and second pore size distributions are different and do not overlap. The first pore size distribution may be, for example, between about 5.9 Angstroms and about 6.3 Angstroms. The second pore size distribution may be, for example, between about 7 Angstroms and about 200 Angstroms, between about 7 Angstroms and about 100 Angstroms, between about 7 Angstroms and about 50 Angstroms, or between about 100 Angstroms and about 200 Angstroms. In some cases, the second catalyst may be mesoporous or non-porous.

The first catalyst may be selective for catalytically reacting the first component or a derivative thereof to produce a fluid product. In addition, the second catalyst may be selective for catalytically reacting the second component or a derivative thereof to produce a fluid nitrogen-containing aromatic product. This method may further comprise pyrolyzing in the reactor at least a portion of the organic material under reaction conditions sufficient to produce one or more pyrolysis products, and catalytically reacting at least a portion of the pyrolysis products with the first and second catalysts to produce the one or more nitrogen-containing aromatic products. In some instances, at least partially deactivated catalyst may also be produced.

In certain embodiments, a method used in combination with the embodiments described herein includes increasing the catalyst to organic material mass ratio in the composition to increase production of identifiable nitrogen-containing aromatic compounds. As illustrated herein, representative but distinct from certain prior catalytic pyrolysis methods, articles and methods described herein can be used to produce discrete, identifiable nitrogen-containing aromatic compounds selected from but not limited to pyrazine, methylpyrazine, pyridine, methylpyridine, aniline, methylaniline, indole, methylindole and combinations thereof. In some embodiments, the reaction chemistry of a catalyst may be affected by adding one or more additional compounds. For example, the addition of a metal to a catalyst may result in a shift in selective formation of specific compounds (e.g., addition of metal to alumina-silicate catalysts may result in the production of more CO). In addition, when the fluidization fluid comprises hydrogen, the amount of coke formed on the catalyst may be decreased. In some embodiments, the catalyst may comprise both silica and alumina (e.g., a zeolite catalyst). The silica and alumina in the catalyst may be present in any suitable molar ratio. In some embodiments, it may be advantageous to employ catalysts with a larger number of moles of silica relative to the number of moles of alumina (i.e., a high silica to alumina molar ratio). The inventors have unexpectedly discovered that high silica to alumina molar ratios, e.g., in combination with embodiments described herein, may result in the formation of a relatively large amount of nitrogen-containing aromatic compound products. For example, in some cases, the feed composition may comprise a silica to alumina molar ratio of at least about 15:1, at least about 30:1, at least about 40:1, at least about 50:1, at least about 75:1, at least about 100:1, at least about 150:1, or higher. In some embodiments, it is advantageous to employ a catalyst with a silica to alumina molar ratio of between about 15:1 and about 200:1, between about 30:1 and about 150:1, between about 50:1 and about 160:1, or between about 100:1 and about 150:1.

In some embodiments, the catalyst and the organic material may be present in any suitable ratio. For example, in cases where the feed composition comprising catalyst and organic material is obtained by e.g., one or more feed streams comprising the catalyst and the organic material or separate catalyst and organic material feed streams (e.g., a circulating fluidized bed reactor), the catalyst and the organic material may be present in any suitable mass ratio. As another example, in cases where the reactor is initially loaded with a mixture of catalyst and organic material (e.g., a batch reactor), the catalyst and organic material may be present in any suitable mass ratio. In some embodiments involving a circulating fluidized bed reactor, the mass ratio of catalyst to organic material in the feed stream (i.e., in a composition comprising a solid catalyst and a solid organic material provided to the reactor) may be at least about 0.01:1, at least about 0.5:1, at least about 1:1, at least about 2:1, at least about 5:1, at least about 10:1, at least about 15:1, at least about 20:1, or higher. In some embodiments involving a circulating fluidized bed reactor, the mass ratio of catalyst to organic material in the feed stream may be less than 0.01:1, less than about 0.5:1, less than about 1:1, less than about 2:1, less than about 5:1, less than about 10:1, less than about 15:1, or less than about 20:1; or from about 0.5:1 to about 20:1, from about 1:1 to about 20:1, or from about 5:1 to about 20:1. Employing a relatively high catalyst to organic material mass ratio may facilitate the introduction of volatile organic compounds, formed from the pyrolysis of the feed material, into the catalyst before they are thermally decomposed to coke. When the mass ratio of catalyst to organic material is less than about 5:1, the products are mainly pyrrole compounds and pyrazine compounds; when the usage amount of the catalyst increases, the selectivities of pyrrole compounds and pyrazine compounds decrease, but those of indole compounds, aniline compounds and pyridine compounds increase. When the ratio of catalyst to organic material is about 10:1, the products are mainly indole compounds and aniline compounds, and the selectivity of pyridine compounds increases as the molar ratio of silica to alumina increases. Without being bound by any theory, this effect may be at least partially due to the presence of a stoichiometric excess of catalyst sites in the reactor. In some embodiments, such as when the reactor is a fixed bed reactor, the space velocity (the weight hourly ratio of liquid feed to catalyst) may be present in any suitable ratio. For example, when the feed is a liquid raw material, it is fed to the reactor in a liquid feed amount/unit volume of the catalyst (WHSV) of 0.05 to 10, e.g., less than about 0.05, less than about 0.1, less than about 0.2, less than about 0.5, less than about 0.8, less than about 1, less than about 1.5, less than about 2, less than about 5, less than about 10. When the WHSV is larger than about 2, the products are mainly pyrrole compounds and pyridine compounds; as the WHSV decreases, the selectivity of pyrrole compounds decreases and the selectivities of indole compounds and aniline compounds increase.

In some embodiments, the articles and methods described herein are configured to selectively produce nitrogen-containing aromatic compounds, e.g., in a single-stage, or alternatively, a multi-stage pyrolysis apparatus. A fluid product may comprise, for example, an amount of nitrogen-containing aromatic compounds that comprise at least about 10 wt %, at least about 15 wt %, at least about 20 wt %, at least about 25 wt %, at least about 30 wt %, at least about 35 wt %, at least about 39 wt %, between about 10 wt % and about 40 wt %, between about 10 wt % and about 35 wt %, between about 15 wt % and about 40 wt %, between about 15 wt % and about 35 wt %, between about 20 wt % and about 40 wt %, between about 20 wt % and about 35 wt %, between about 25 wt % and about 40 wt %, between about 25 wt % and about 35 wt %, between about 30 wt % and about 40 wt %, or between about 30 wt % and about 35 wt % of the total reaction products of the solid organic material. The yields of the compounds described above are calculated as carbon yields, that is, the carbon yield is calculated by dividing the moles of carbon in the product by moles of carbon in the feed. The selectivity is calculated as the moles of carbon in a given product divided by the moles of carbon in all products (excluding CO, $CO_2$, and coke (e.g., solid coke remaining on the catalyst)). It should be noted that one of ordinary skill in the art will be able to convert between weight percentages and carbon yield. The amount of carbon in a carbonaceous material feed may be determined, for example, via chemical analysis. In addition, the carbon percentage of each of the reaction products may be calculated using their molecular formulas. As used herein, the term "nitrogen-containing aromatic compound" is used to refer to a hydrocarbon compound comprising one or more cyclic groups with aromaticity, for example, a single aromatic ring system (e.g., pyrazine, pyridine, pyrrole, etc.) and a fused polycyclic aromatic ring system (e.g. indole, etc.). Examples of nitrogen-containing aromatic compounds include, but are not limited to, one or more of pyrazine, 2-methylpyrazine, 2,5-dimethylpyrazine, 2,6-dimethylpyrazine, pyridine, 2-methylpyridine, 3-methylpyridine, 4-methylpyridine, dimethylpyridine, pyrrole, 2-methylpyrrole, 3-methylpyrrole, 2,5-dimethylpyrrole, indole, 1-methylindole, 2-methylindole, 3-methylindole, 2,8-dimethylindole, aniline, o-methylaniline, m-methylaniline, p-methylaniline, dimethylaniline, etc., or combinations thereof. In some embodiments, the nitrogen-containing aromatic compounds containing a single ring and/or more rings may be produced. The nitrogen-containing aromatic compounds may have, for example, carbon numbers of C5-C14, C6-C8, C6-C12, C8-C12, or C10-C14, and nitrogen numbers of N1-N2, N3-N4, or N5-N6. Pyrazine compounds may be used as important medical intermediates and intermediates of fragrances and flavors, and are also a kind of fine chemicals with high additional values. Pyridine and derivatives thereof are very important chemical intermediates and are widely used in industries of medicines, pesticides, fodders, synthetic rubbers and printing and dyeing, and may also be used in the production of surfactants and food additives. As important intermediates of fine chemical products, pyrrole compounds have wide application in the fields of medicines, foods, pesticides, commodity chemicals, coatings, weaving, printing and dyeing, paper making, photosensitive materials, polymer materials, etc. Indole is an essential chemical raw material and is widely used in various fields of medicines, pesticides, dyes, foods, flavors, etc. Aniline is an important industrial chemical and may be used as raw material for producing rubber vulcanization accelerator, dye, mordant, drug, explosive and methylene diphenyl diisocyanate (MDI).

In some embodiments of the invention, the above nitrogen-containing aromatic compounds may be separated by methods well known in the art. For example, separation methods, such as distillation (including normal-pressure distillation, reduced-pressure distillation, molecular distillation), rectification, column chromatography, acid extraction method, ion exchange chromatography, extraction method, etc., may be used. In this invention, different compounds may be selectively prepared according to different catalytic methods. Firstly, distillation may be performed according to physical parameters of the compounds themselves (see Table 1), and fractions at different temperatures, such as pyrazine fractions, pyrrole fractions, pyridine fractions, aniline fractions, and indole fractions, may be obtained. Rectification is then performed to separate the product so as to obtain a product with a higher purity. Some compounds have very close boiling points, such as 2-methylindole and 3-methylindole, and they may be separated according to the magnitude of the polarity thereof using column chromatography and the like. Some compounds have close boiling points but greatly different molecular weights from each other, and a separation distillation method may be used. Furthermore, in some embodiments, the catalyst may be chosen to facilitate selective production of nitrogen-containing aromatic compounds. For example, ZSM-5 may, in some cases, preferentially produce relatively higher amount of nitrogen-containing aromatic compounds. In some cases, catalysts that include Bronsted acid sites may facilitate selective production nitrogen-containing aromatic compounds. In addition, catalysts with well-ordered pore structures may facilitate selective production of nitrogen-containing aromatic compounds. For example, in some embodiments, catalysts with average pore diameters between about 5.9 Angstroms and about 6.3 Angstroms may be particularly useful in producing nitrogen-containing aromatic compounds. In addition, catalysts with average pore diameters between about 7 Angstroms and about 8 Angstroms may be useful in producing olefins. In some embodiments, a combination of one or more of the above process parameters may be employed to facilitate selective production of nitrogen-containing aromatic compounds. The ratio of nitrogen-containing aromatic compounds to olefins produced may be, for example, between about 0.1:1 and about 10:1, between about 0.2:1 and about 5:1, between about 0.5:1 and about 2:1, between about 0.1:1 and about 0.5:1, between about 0.5:1 and about 1:1, between about 1:1 and about 5:1, or between about 5:1 and about 10:1.

EXAMPLES

In the following Examples, gas chromatography and gas chromatography-mass spectrometry were mainly used in the characterization of reaction products. A GC-1690 gas chromatograph of Hangzhou Kexiao Instrument was mainly used, in which a 30 m×0.25 mm×0.25 μm chromatographic column was used and the temperature was programmed to 280° C. at 10° C./min. A Thermo Trace GC Ultra with an ISQ i mass spectrometer, United States, was mainly used as a gas chromatography-mass spectrometry instrument, in which a TR-35MS chromatographic column (30 m×0.25 mm×25 μm) was used, and the detection method was as follows: after maintaining at 40° C. for 3 min, the temperature was increased to 180° C. at 5° C./min, and then the temperature was increased to 280° C. at 10° C./min.

The following non-limiting examples and data are intended to illustrate various aspects and characteristics related to the methods and/or compositions of the invention, including the selective production of various compounds by the pyrolytic methods described herein, rather than exemplifying the full scope of the invention. Compared to the prior art, the methods and compositions of this invention provide surprising and unexpected results and data. While the effects of this invention are illustrated by the use of several catalysts and raw materials, it will be understood by those skilled in the art that comparable results are obtainable with various other catalysts and/or raw materials, as are commensurate with the scope of this invention.

Example 1

Figure 5:
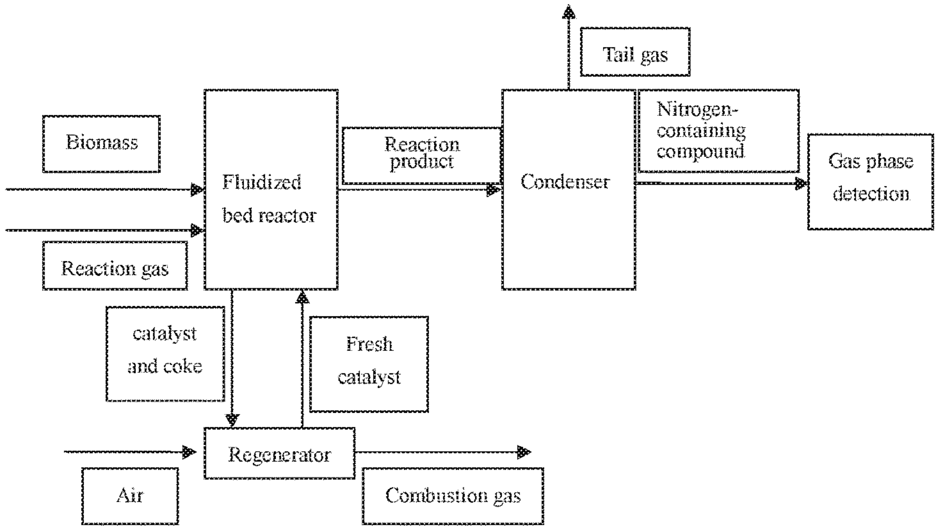
FIG. 5 is a flow chart of the reaction model shown in Example 1.

In this example, a quartz tubular reactor with a diameter of 34 mm and a length of 300 mm was used. In the reactor, the catalyst was supported by quartz wool. The quartz reactor was placed in a temperature-controlled furnace. During operation, ammonia gas was used as a carrier gas, and its flow rate was controlled by a gas flowmeter. $NH_3$ or a mixed gas of $NH_3/N_2$ or $NH_3/He$ was used as a carrier gas in this experiment. Powdered raw materials flowed from the opening of the quartz tube into the pyrolysis interface together with a carrier gas stream. Liquid products flowed from the reactor to a condenser, and gas products were collected in gas-sampling bags. Liquid and gas products were analyzed using a gas chromatograph (a model reaction diagram can be seen in FIG. 5). As a representative of several embodiments, the catalytic pyrolysis experiments in Examples 1-10 were conducted with powdered catalyst and feed (<140 mesh size). Unless otherwise illustrated in this Example, the reaction conditions were described as above.

Powdered reactants were prepared by physically mixing a carbohydrate feed and a catalyst. A physical mixture of glucose having a catalyst-to-feed mass ratio of 2 was prepared with glucose and HZSM-5 (Si/Al=25). Cellobiose/HZSM-5, cellulose/HZSM-5, xylose/HZSM-5, xylitol/HZSM-5, xylan/HZSM-5, chitosan/HZSM-5, chitin/HZSM-5, sucrose/HZSM-5, fructose/HZSM-5 having catalyst-to-feed mass ratios of 2 were also prepared, and product distribution measured by GC/MS can be seen in FIG. 1.

TABLE 2

Summary of pyrolysis experiments

| Feed | Catalyst | Mass ratio of catalyst to feed | Heating temperature (° C.) | Gas flow rate (ml/min) | Yield of nitrogen-containing heterocyclic compounds (%) | Yield of nitrogen-free compounds (%) | Yield of gas (%) | Yield of coke (%) | Yield of total carbon (%) | Unidentified (%) |
|---|---|---|---|---|---|---|---|---|---|---|
| Glucose | HZSM-5 | 2 | 500 | 200 | 16.4 | <1 | 30.5 | 40.1 | 87.0 | 13.0 |
| Cellobiose | HZSM-5 | 2 | 500 | 250 | 14.2 | <1 | 26.4 | 37.6 | 78.2 | 21.8 |
| Cellulose | HZSM-5 | 2 | 500 | 150 | 13.5 | <1 | 24.3 | 39.6 | 77.4 | 22.6 |
| Xylose | HZSM-5 | 2 | 500 | 300 | 19.7 | <1 | 23.8 | 36.5 | 80 | 20.0 |
| Xylitol | HZSM-5 | 2 | 500 | 250 | 21.5 | <1 | 25.2 | 45.2 | 91.9 | 8.1 |
| Xylan | HZSM-5 | 2 | 500 | 150 | 20.2 | <1 | 28.5 | 43.9 | 92.6 | 7.4 |
| Fructose | HZSM-5 | 2 | 500 | 200 | 26.6 | <1 | 22.7 | 35.2 | 84.5 | 15.5 |
| Sucrose | HZSM-5 | 2 | 500 | 250 | 20.8 | <1 | 28.9 | 37.1 | 86.8 | 13.2 |

TABLE 2-continued

| Summary of pyrolysis experiments | | | | | | | | | | |
|---|---|---|---|---|---|---|---|---|---|---|
| Feed | Catalyst | Mass ratio of catalyst to feed | Heating temperature (° C.) | Gas flow rate (ml/min) | Yield of nitrogen-containing heterocyclic compounds (%) | Yield of nitrogen-free compounds (%) | Yield of gas (%) | Yield of coke (%) | Yield of total carbon (%) | Unidentified (%) |
| Chitosan | HZSM-5 | 2 | 500 | 200 | 22.8 | <1 | 30.2 | 36.1 | 89.1 | 10.9 |
| Chitin | HZSM-5 | 2 | 500 | 200 | 21.6 | <1 | 31.3 | 38.2 | 91.1 | 8.9 |
| Starch | HZSM-5 | 2 | 500 | 200 | 22.5 | <1 | 32.4 | 36.7 | 91.6 | 8.4 |

Example 2

The addition of catalyst to the pyrolysis process significantly decreased coke formation and increased the conversion to thermally stable products. Six different catalysts were tested for catalytic pyrolysis of glucose, including: γ-alumina (γ-$Al_2O_3$), silica-alumina ($SiO_2$—$Al_2O_3$), tungsten oxide-zirconium oxide ($WO_3/ZrO_2$), sulfate-zirconium dioxide ($SO_4^{2-}/ZrO_2$), MCM-41, HZSM-5 (Si/Al=63). Powdered reactants were prepared by physically mixing the carbohydrate feed and the catalyst. The usage amount ratio of the catalyst to glucose in this experiment was 2, the reaction temperature was 550° C., and the gas flow rate was 200 ml/min. The catalyst and glucose was mixed and was then ground to powder. The structure of the catalyst greatly changes the product selectivity, and the selectivity of pyrrole compounds may be increased by using HZSM-5 catalyst and the selectivity of pyrazine compounds may be increased by using $SO_4^{2-}/ZrO_2$.

TABLE 3

| Catalytic pyrolysis of glucose using different catalysts | | | | | | | | |
|---|---|---|---|---|---|---|---|---|
| | Conversion ratio (wt %) | | Conversion ratio of nitrogen-containing | Carbon selectivity (%) | | | | |
| Catalyst | Liquid + Gas | Solid | compounds (C %) Stable compounds | Pyrazine compounds | Pyrrole compounds | Other compounds | $CO_2$ | CO |
| None | 56.5 | 43.5 | 2 | <1 | <1 | 74 | 8 | 18 |
| γ-$Al_2O_3$ | 60.8 | 39.8 | 10 | 8 | 60 | 7 | 12 | 13 |
| $SiO_2$—$Al_2O_3$ | 65.2 | 34.8 | 12 | 10 | 55 | 2 | 20 | 13 |
| $WO_3/ZrO_2$ | 66.3 | 33.7 | 15 | 40 | 32 | 2 | 16 | 10 |
| $SO_4^{2-}/ZrO_2$ | 70.8 | 29.2 | 20 | 52 | 19 | 2 | 18 | 9 |
| MCM-41 | 64.1 | 35.9 | 14 | 15 | 48 | <1 | 12 | 24 |
| HZSM-5 | 65.9 | 34.1 | 16 | 10 | 60 | <1 | 11 | 19 |

Example 3

The effect of reaction temperature on product yield was investigated in this Example. Table 4 and Table 5 indicated that nitrogen-containing heterocyclic products increased to some extent as the temperature increased. However, as the temperature increased, the selectivity of pyrrole compounds decreased to some extent and the selectivities of indole compounds and aniline compounds increased to some extent.

TABLE 4

| Effect of different pyrolysis temperatures on glucose pyrolysis products | | | | | | | | | | |
|---|---|---|---|---|---|---|---|---|---|---|
| Feed | Catalyst | Mass ratio of catalyst to feed | Heating temperature (° C.) | Gas flow rate (ml/min) | Yield of nitrogen-containing heterocyclic compounds (%) | Yield of nitrogen-free compounds (%) | Yield of gas (%) | Yield of coke (%) | Yield of total carbon (%) | Unidentified (%) |
| Glucose | HZSM-5 | 2 | 300 | 200 | 9.7 | <1 | 17.8 | 60.1 | 87.6 | 12.4 |
| Glucose | HZSM-5 | 2 | 400 | 200 | 14.8 | <1 | 22.3 | 42.5 | 79.6 | 20.4 |
| Glucose | HZSM-5 | 2 | 500 | 200 | 16.4 | <1 | 30.5 | 40.1 | 87.0 | 13.0 |
| Glucose | HZSM-5 | 2 | 600 | 200 | 14.3 | <1 | 40.9 | 33.1 | 88.3 | 11.3 |
| Glucose | HZSM-5 | 2 | 700 | 200 | 12.3 | <1 | 45.9 | 28.1 | 86.3 | 13.7 |

TABLE 5

Distribution of catalytic pyrolysis products of glucose at different temperatures

| Temperature | Carbon yield of nitrogen-containing heterocyclic compounds (C %) | Carbon selectivity (C %) Pyrazine | Methyl pyrazine | Pyrrole | Pyridine | Methyl pyrrole | Indole | Methyl indole | Aniline | Methyl aniline |
|---|---|---|---|---|---|---|---|---|---|---|
| 300 | 9.7 | 8 | 3 | 73 | <1 | 16 | <1 | <1 | <1 | <1 |
| 400 | 14.8 | 10 | 6 | 66 | <1 | 19 | <1 | <1 | <1 | <1 |
| 500 | 16.4 | 12 | 7 | 56 | <1 | 20 | 2 | 3 | <1 | <1 |
| 600 | 14.3 | 15 | 8 | 46 | 3 | 16 | 5 | 5 | <1 | <1 |
| 700 | 12.3 | 16 | 7 | 42 | 6 | 13 | 10 | 4 | 2 | <1 |

Example 4

The effect of the silica to alumina molar ratio of catalyst was investigated in this Example. The conditions for these experiments were as follows: catalyst/feed mass ratio was 5; catalyst: HZSM-5; reaction temperature: 550° C.; and carrier gas flow rate: 200 ml/min. Glucose was used as raw materials for these experiments. Table 6 showed the effect of different silica to alumina molar ratios on the product selectivity for catalytic pyrolysis of glucose. As shown in Table 6, a low silicon-to-aluminum ratio may improve the selectivity of pyrrole, and the increase of the silicon to aluminum ratio was favorable to improve the selectivity of pyridine compounds.

TABLE 6

Summary about silica to alumina molar ratio of catalyst

| $SiO_2$:$Al_2O_3$ ratio | Carbon yield of nitrogen-containing heterocyclic compounds (C %) | Carbon selectivity (C %) Pyrazine | Methyl pyrazine | Pyridine | Pyrrole | Methyl pyrrole | Indole | Methyl indole | Aniline | Methyl aniline |
|---|---|---|---|---|---|---|---|---|---|---|
| 25 | 16.4 | 12 | 7 | 10 | 46 | 20 | 2 | 3 | <1 | <1 |
| 50 | 15.5 | 14 | 6 | 14 | 44 | 16 | 3 | 3 | <1 | <1 |
| 63 | 13.6 | 13 | 8 | 18 | 40 | 15 | 3 | 3 | <1 | <1 |
| 80 | 12.9 | 12 | 6 | 23 | 39 | 23 | 4 | 3 | <1 | <1 |
| 100 | 13.2 | 11 | 7 | 26 | 30 | 15 | 2 | 2 | <1 | <1 |
| 150 | 12.8 | 6 | 6 | 29 | 30 | 23 | 2 | 3 | <1 | <1 |
| 200 | 12.5 | 8 | 5 | 33 | 25 | 23 | 2 | 3 | <1 | <1 |

Example 5

The effects of the mass ratio of catalyst to glucose feed on product yield and product distribution were investigated in this Example. The conditions for these experiments were as follows: catalyst: HZSM-5; reaction temperature: 500° C.; and carrier gas flow rate: 150 ml/min. Glucose was used as raw materials for these experiments. Table 7 showed the product selectivity for catalytic pyrolysis of glucose as a function of the silica to alumina molar ratio. As shown in Table 7, the ratio of catalyst to feed was 1, 2, 5, 10, 15, 20, respectively. From Tables 7 and 8, it was indicated that pyrrole products and pyrazine products gradually decreased and indole products gradually increased, as the usage amount of the catalyst increased.

TABLE 7

Summary of pyrolysis experiments

| Feed | Catalyst | Mass ratio of catalyst to feed | Heating temperature (° C.) | Gas flow rate (ml/min) | Yield of nitrogen-containing heterocyclic compounds (%) | Yield of nitrogen-free compounds (%) | Yield of gas (%) | Yield of coke (%) | Yield of total carbon (%) | Unidentified (%) |
|---|---|---|---|---|---|---|---|---|---|---|
| Glucose | HZSM-5 | 1 | 500 | 200 | 12.1 | <1 | 34.7 | 33.4 | 80.2 | 19.2 |
| Glucose | HZSM-5 | 2 | 500 | 200 | 16.4 | <1 | 30.5 | 40.1 | 87.0 | 13.0 |
| Glucose | HZSM-5 | 5 | 500 | 200 | 19.8 | <1 | 28.2 | 38.2 | 86.2 | 13.8 |
| Glucose | HZSM-5 | 10 | 500 | 200 | 12.9 | <1 | 36.6 | 37.3 | 87.8 | 12.2 |
| Glucose | HZSM-5 | 15 | 500 | 200 | 12.6 | <1 | 39.4 | 33.5 | 85.5 | 14.5 |
| Glucose | HZSM-5 | 20 | 500 | 200 | 9.8 | <1 | 41.2 | 31.3 | 82.3 | 17.7 |

TABLE 8

Effect of usage amount ratio of catalyst to glucose on products

| Mass ratio of catalyst to feed | Carbon yield of nitrogen-containing heterocyclic compounds (C %) | Carbon selectivity (C %) Pyrazine | Methyl pyrazine | Pyrrole | Methyl pyrrole | Indole | Methyl indole | Aniline | Methyl aniline |
|---|---|---|---|---|---|---|---|---|---|
| 1 | 12.1 | 15 | 5 | 51 | 19 | <1 | <1 | <1 | <1 |
| 2 | 16.4 | 12 | 7 | 56 | 20 | 2 | 3 | <1 | <1 |
| 5 | 19.8 | 10 | 4 | 55 | 22 | 3 | 4 | <1 | <1 |
| 10 | 12.9 | 9 | 6 | 48 | 19 | 10 | 8 | <1 | <1 |
| 15 | 12.6 | 8 | 4 | 40 | 15 | 20 | 13 | <1 | <1 |
| 20 | 9.8 | 5 | 2 | 30 | 8 | 28 | 27 | <1 | <1 |

Example 6

The effects of the ratio of $NH_3$ to $N_2$ in carrier gas on product yield and product distribution were investigated in this Example. The conditions for these experiments were as follows: catalyst: HZSM-5; reaction temperature: 500° C.; carrier gas: a mixed gas of $NH_3$ and $N_2$; and carrier gas flow rate: 250 ml/min. Glucose was used as raw materials for these experiments. The $NH_3/N_2$ ratios of the carrier gas in this experiment was 0:1, 1:19, 1:9, 1:4, 1:1, 4:1, 19:1 and 1:0. Table 9 showed the effects of distribution of $NH_3$ and $N_2$ on product selectivity for catalytic pyrolysis of glucose. From Table 9, it was indicated there was an important relationship between nitrogen-containing compounds in the product and $NH_3$ in the carrier gas, and as the amount of $NH_3$ increased, the amount of corresponding nitrogen-containing compounds also increased.

TABLE 9

Summary of pyrolysis experiments

| Feed | Catalyst | Volume ratio of $NH_3$ to $N_2$ | Heating temperature (° C.) | Gas flow rate (ml/min) | Yield of nitrogen-containing heterocyclic compounds (%) | Yield of nitrogen-free compounds (%) | Yield of gas (%) | Yield of coke (%) | Yield of total carbon (%) |
|---|---|---|---|---|---|---|---|---|---|
| Glucose | HZSM-5 | 0:1 | 500 | 250 | <1 | 13.8 | 33.4 | 34.7 | 81.9 |
| Glucose | HZSM-5 | 1:19 | 500 | 250 | 1.1 | 12.7 | 32.5 | 37.1 | 83.4 |
| Glucose | HZSM-5 | 1:9 | 500 | 250 | 2.5 | 11.2 | 33.8 | 36.2 | 83.7 |
| Glucose | HZSM-5 | 1:4 | 500 | 250 | 4.6 | 9.5 | 36.9 | 36.4 | 87.4 |
| Glucose | HZSM-5 | 1:1 | 500 | 250 | 8.9 | 1.4 | 38.9 | 35.8 | 85.0 |
| Glucose | HZSM-5 | 4:1 | 500 | 250 | 12.3 | <1 | 37.2 | 36.0 | 85.5 |
| Glucose | HZSM-5 | 19:1 | 500 | 250 | 12.6 | <1 | 36.9 | 36.3 | 85.8 |
| Glucose | HZSM-5 | 1:0 | 500 | 250 | 12.5 | <1 | 35.3 | 35.7 | 83.5 |

Example 7

Metal impregnation in the catalyst may affect product yield. Impregnation of HZSM-5 (silica to alumina molar ratio of 25) pores with metals shifted the product selectivity toward CO and $CO_2$, showing that metals can influence the chemical reaction. Not wishing to be bound by any theory, the metals may increase decarbonylation and/or decarboxylation reaction rates. The following metals were tested. In addition to the metal described below, this patent also included other metals, such as In, Ru, Rh, Ir, Pt, Pd, Au, Re, Tl, and lanthanide. Table 10 summarized the results obtained from the catalytic pyrolysis of glucose on metal doped HZSM-5. Two different methods were employed to dope metal into metal HZSM-5: dry/wet impregnation and ion exchange. Catalysts impregnated using the ion exchange method produced higher yields of pyrrole compounds and indole compounds compared to catalysts impregnated using the dry/wet impregnation method.

TABLE 10

Summary of metal addition of HZSM-5

| Catalyst | Load of metal (wt %) | Preparation method | Yield of nitrogen-containing heterocyclic compounds (C %) | Yield of nitrogen-free compounds (C %) | Yield of gas (C %) | Yield of gas coke (C %) |
|---|---|---|---|---|---|---|
| Cu-HZSM-5 | 6.4 | Solid ion exchange | 7.9 | <1 | 50.5 | 31.8 |
| Mn-HZSM-5 | 5 | Wet impregnation | 11.2 | <1 | 43.8 | 44.0 |
| Mn-HZSM-5 | 5 | Ion exchange | 20.1 | <1 | 28.4 | 34.1 |
| Co-HZSM-5 | 5 | Wet impregnation | 9.8 | <1 | 66.9 | 18.8 |
| Fe-HZSM-5 | 5 | Dry impregnation | 16.9 | <1 | 36.3 | 41.8 |
| Ni-HZSM-5 | 5 | Wet impregnation | 6.6 | <1 | 71.2 | 11.3 |
| Zn-HZSM-5 | 5 | Wet impregnation | 19.3 | <1 | 35.1 | 36.9 |
| Zn-HZSM-5 | 5 | Ion exchange | 25.4 | <1 | 38.7 | 31.4 |
| Ga-HZSM-5 | 5 | Wet impregnation | 23.5 | <1 | 26.0 | 48.0 |
| Ga-HZSM-5 | 5 | Ion exchange | 25.9 | <1 | 35.9 | 23.0 |
| Pt-HZSM-5 | 5 | Wet impregnation | 15.3 | <1 | 48.3 | 23.5 |

Example 8

The catalyst pore size also affected the yield of nitrogen-containing heterocyclic compounds. Glucose was used as raw materials for these experiments. Table 11 represented carbon yield data of catalytic pyrolysis of glucose over several zeolites with different structures. The conditions for these experiments were as follows: catalysts as shown in the Table below; reaction temperature of 500° C.; carrier gas flow rate of 200 ml/min; and catalyst to glucose feed ratio of 5. From the results of Table 11, it could be seen that the pore size close to that of ZSM-5 was favorable to the generation of nitrogen-containing heterocyclic compounds.

TABLE 11

Summary of different structures of catalysts

| Zeolite | structure | pore size | Yield of nitrogen-containing compounds (C %) | Yield of nitrogen-free compounds (C %) | Yield of gas (C %) | Yield of coke (C %) |
|---|---|---|---|---|---|---|
| ZK-5 | Cubic | 3.9 * 3.9 | 1.2 | 2.0 | 43.4 | 47.2 |
| ZSM-23 | Rhombic | 4.5 * 5.2 | 8.2 | <1 | 28.2 | 43.6 |
| SSZ-20 | Rhombic | 4.6 * 5.7 | 7.9 | <1 | 20.7 | 36.1 |
| β-zeolite | Tetragonal | 6.6 * 6.7<br>5.6 * 5.6 | 4.5 | <1 | 27.9 | 62.9 |
| Y-zeolite | Cubic | 7.4 * 7.4 | 2.1 | <1 | 16.2 | 80.1 |
| MCM-41 | Hexagonal | 3.5 * 3.5 | 8.5 | <1 | 31.2 | 50.9 |

Example 9

Biomass in nature was also used as raw materials in experiments to prepare pyrrole compounds and indole compounds by catalytic pyrolysis. Table 12 summarized the results for catalytic pyrolysis of naturally occurred biomass. Nitrogen-containing compounds, nitrogen-free compounds, gas, and coke were generated by catalytic pyrolysis of wood, bagasse, corn straws, waste paper, rape seed cakes, microalgae using HZSM-5 catalyst. These results indicated that nitrogen-containing compounds such as pyrrole compounds and indole compounds, etc., may be prepared by catalytic pyrolysis of naturally occurred biomass.

TABLE 12

Catalytic pyrolysis of naturally occurred biomass

| Raw material | Catalyst | Mass ratio of catalyst to raw material | Heating temperature (° C.) | Yield of nitrogen-containing compounds (C %) | Yield of nitrogen-free compounds (C %) | Yield of gas (C %) | Yield of coke (C %) |
|---|---|---|---|---|---|---|---|
| Wood | HZSM-5 | 2 | 500 | 13.2 | 4.6 | 16.5 | 50.2 |
| Bagasse | HZSM-5 | 2 | 500 | 12.4 | 2.5 | 25.8 | 45.6 |
| Corn straws | HZSM-5 | 2 | 500 | 11.6 | 2.9 | 19.9 | 39.3 |
| Rape seed cakes | HZSM-5 | 2 | 500 | 16.6 | <1 | 30.5 | 36.1 |
| Waste paper | HZSM-5 | 2 | 500 | 14.5 | <1 | 28.8 | 38.9 |
| Microalgae | HZSM-5 | 2 | 500 | 15.5 | <1 | 29.4 | 37.8 |

Example 10

Powdered reactants were prepared by physically mixing the carbohydrate feed and the catalyst. Mixtures of HZSM-5/glucose, HZSM-5/cellulose, HZSM-5/xylose, xylitol/HZSM-5, xylan/HZSM-5, fructose/HZSM-5, sucrose/HZSM-5, chitosan/HZSM-5, chitin/HZSM-5 each having a catalyst-to-feed mass ratio of 10 were prepared and were used for producing indole products and aniline compounds. The conditions for these experiments were as follows: catalyst: HZSM-5; ratio of catalyst to feed: 10; and feed speed: 0.2 g/min. GC/MS graphs of product distribution can be seen in FIG. 2.

TABLE 13

Summary of experiments for producing indole and aniline compounds

| Feed | Catalyst | Mass ratio of catalyst to feed | Heating temperature (° C.) | Gas flow rate (ml/min) | Yield of nitrogen-containing heterocyclic compounds (%) | Yield of nitrogen-free compounds (%) | Yield of gas (C %) | Yield of coke (%) |
|---|---|---|---|---|---|---|---|---|
| Glucose | HZSM-5 | 10 | 600 | 100 | 16.4 | <1 | 40.5 | 35.1 |
| Cellulose | HZSM-5 | 10 | 600 | 100 | 13.2 | <1 | 33.4 | 32.6 |
| Xylose | HZSM-5 | 10 | 600 | 100 | 14.5 | <1 | 31.3 | 34.6 |
| Glucose | HZSM-5 | 10 | 600 | 50 | 18.4 | <1 | 39.5 | 37.1 |
| Xylitol | HZSM-5 | 10 | 550 | 100 | 15.3 | <1 | 38.2 | 33.8 |
| Xylan | HZSM-5 | 10 | 550 | 100 | 11.7 | <1 | 39.4 | 35.8 |
| Fructose | HZSM-5 | 10 | 600 | 100 | 19.6 | <1 | 33.5 | 34.2 |
| Sucrose | HZSM-5 | 10 | 600 | 100 | 15.8 | <1 | 35.7 | 34.6 |
| Chitosan | HZSM-5 | 10 | 600 | 100 | 17.6 | <1 | 39.6 | 37.5 |
| Chitin | HZSM-5 | 10 | 600 | 100 | 13.9 | <1 | 36.8 | 40.2 |

Example 11

In the Examples described above, the manner of fluidized bed was mainly used as the test method, and the catalyst and raw materials were mixed and ground and were then prepared into powders with a mesh size of 140 for feeding. The manner of fixed bed may also be employed in this experiment for feeding, and test manner was as follows. In this example, a quartz tubular reactor with a diameter of 34 mm and a length of 300 mm was used. The reactor was charged with HZSM-5 catalyst to produce a fixed bed, and both ends of the catalyst were supported by quartz wool. The quartz reactor was placed in a temperature-controlled furnace. During operation, ammonia gas was used as a carrier gas, and its flow rate was controlled by a gas flowmeter. Powdered raw materials flowed from the opening of the quartz tube into the pyrolysis interface together with an ammonia carrier gas stream. Liquid products flowed from the reactor to a condenser, and gas products were collected in a gas-sampling bag. Liquid and gas products were analyzed using a gas chromatograph.

In this Example, a fixed bed was mainly used to prepare pyrazine compounds, pyrrole compounds, indole compounds and aniline compounds, respectively. The experimental method was as follows. Fixed bed reactors with catalyst mass of 2 g, 5 g and 10 g respectively were used. Reaction raw materials were passed into a catalyst bed layer together with a carrier gas. Liquid products flowed to a condenser, and gas products were collected in a gas-sampling bag. Liquid and gas products were analyzed using a gas chromatograph. Table 14 indicated the preparation of nitrogen-containing compounds, and Table 15 indicated the carbon selectivities of various compounds in the liquid.

TABLE 14

Summary of preparation of nitrogen-containing compounds by fixed bed

| Feed | Catalyst | Catalyst bed layer | Heating temperature (° C.) | Gas flow rate (ml/min) | Yield of nitrogen-containing heterocyclic compounds (C %) | Yield of nitrogen-free compounds (C %) | Yield of gas (C %) | Yield of coke (C %) |
|---|---|---|---|---|---|---|---|---|
| Glucose | HZSM-5 | 2 | 500 | 200 | 9.4 | <1 | 42.5 | 38.1 |
| Glucose | HZSM-5 | 5 | 600 | 200 | 8.2 | <1 | 38.4 | 40.6 |
| Glucose | HZSM-5 | 10 | 600 | 200 | 7.5 | <1 | 39.3 | 42.6 |
| Glucose | HZSM-5 | 20 | 600 | 200 | 6.8 | 1.5 | 40 | 44.8 |

TABLE 15

Product selectivities of fixed bed pyrolysis products

| Mass ratio of catalyst to feed | Carbon yield of nitrogen-containing heterocyclic compounds (C %) | Carbon selectivity (C %) | | | | | | | |
|---|---|---|---|---|---|---|---|---|---|
| | | Pyrazine | Methyl pyrazine | Pyrrole | Methyl pyrrole | Indole | Methyl indole | Aniline | Methyl aniline |
| 2 | 9.4 | 13 | 5 | 66 | 16 | <1 | <1 | <1 | <1 |
| 5 | 8.2 | <1 | <1 | 3 | <1 | 75 | 12 | <1 | <1 |
| 10 | 7.5 | <1 | <1 | <1 | <1 | 38 | 9 | 48 | 5 |
| 20 | 6.8 | <1 | <1 | <1 | <1 | 13 | 2 | 71 | 14 |

Example 13

In the Examples described above, the manner of solid feeding was mainly described, including the flow bed and fixed bed reaction manners after mixing of the catalyst and the reaction raw materials. This example describes the use of a fixed bed, flow reactor system. In this example, a quartz tubular reactor with a diameter of 10 mm and a length of 250 mm was used. In this reactor, a certain amount (0.01 g-2.5 g) of HZSM-5 catalyst was loaded to produce a fixed bed, which was supported by quartz wool. The quartz reactor was placed in a high-temperature furnace. $NH_3$ or a mixed gas of $NH_3/N_2$, $NH_3/He$ was used as a carrier gas in this experiment. The reaction raw materials were liquid raw materials and the flow rate thereof was controlled by a mass flow controller. Liquid raw materials were introduced into the carrier gas by a syringe pump and were passed into the reactor. Liquid products flowed from the reactor to a condenser, and gas products were collected in a gas-sampling bag. Liquid and gas products were analyzed using a gas chromatograph.

In this Example, the weight hourly space velocity (WHSV) was calculated by dividing liquid feed mass (g/h) by catalyst weight (g). The carbon yield was calculated by dividing the moles of the carbon in a product by the moles of carbon fed to the reactor.

As a representative of several embodiments, catalytic pyrolysis tests described in Examples 14-16 were conducted. Unless otherwise illustrated in the Examples, these reaction conditions were described as above.

Example 14

Figure 6:
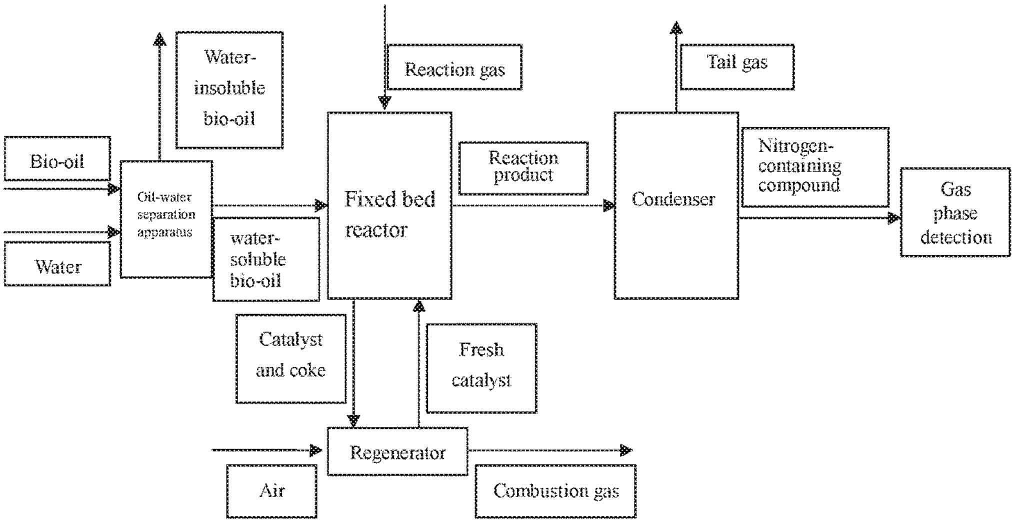
FIG. 6 is a schematic flow chart of the reaction of water-soluble bio-oil (Example 14) by catalytic pyrolysis.

The effects of liquid reaction and raw materials were mainly investigated in this Example. The conditions for these experiments were as follows: catalyst: ZSM-5; catalyst usage amount: 1 g; reaction temperature: 500° C.; carrier gas: $NH_3$; and carrier gas flow rate: 40 ml/min. In this experiment, the cellulose bio-oil and the bio-oils were obtained from pyrolysis of cellulose, poplar wood, microalgae, etc., under the condition of 500° C., respectively. Pine wood and cellulose were representatives in this Example, and other biomass was also applicable to the requirement for the raw materials in this experiment. Water-soluble bio-oils were mainly derived from water separated products of bio-oils. Bio-oils and water were formulated into a mixture at a ratio of 1:4, and then the mixture was centrifuged in a centrifuge at a rotational speed of 1000 revolutions per minute for 20 minutes. The upper layer, which is water-soluble bio-oils, was decanted, and the remaining portion was water-insoluble bio-oils. (The flow chart of the reaction model can be seen in FIG. 6)

TABLE 16

Summary of pyrolysis experiments

| Feed | Space velocity WHSV (h−1) | Yield of nitrogen-containing heterocyclic compounds[2] (C %) | Yield of nitrogen-free compounds (C %) | Yield of gas (C %) | Yield of coke (C %) | Yield of total carbon (C %) |
|---|---|---|---|---|---|---|
| Aqueous glucose solution | 2 | 23.8 | <1 | 38.9 | 17.1 | 79.8 |
| Methylfuran | 2 | 45.4 | <1 | 34.5 | 12.3 | 92.2 |
| 2,5-dimethylfuran | 2 | 46.2 | <1 | 35.4 | 11.6 | 93.2 |
| Furfural | 2 | 18.5 | <1 | 30.3 | 39.6 | 88.4 |
| 5-hydroxymethylfurfural | 2 | 19.5 | <1 | 31.2 | 40.2 | 90.9 |
| 5-methylfurfural | 2 | 39.2 | <1 | 34.5 | 13.9 | 87.6 |
| γ-valerolactone | 2 | 38.3 | <1 | 33.8 | 19.5 | 91.6 |
| Cellulose bio-oil | 2 | 24.8 | <1 | 34.9 | 33.1 | 92.8 |
| Water-soluble bio-oil | 2 | 20.8 | 1.6 | 28.9 | 37.1 | 88.4 |
| Bio-oil[1] | 2 | 10.2 | 8.9 | 29.3 | 32.6 | 81.0 |

[1]See FIG. 4 for the distribution of catalytic pyrolysis products of bio-oils.
[2]Nitrogen-containing compounds include pyrrole, pyridine, indole, and aniline compounds.

Example 15

The effect of WHSV on the product distribution was investigated mainly by using furan as a model compound in this Example. The conditions for experiments were as follows: catalyst: HZSM-5 (Si/Al=25); catalyst usage amount: 1 g; reaction temperature: 500° C.; carrier gas: $NH_3$; and carrier gas flow rate: 20 ml/min. From Table 17, it could be known that as the WHSV decreased, the selectivities of pyrrole and methylpyrrole decreased and the selectivities of pyridine compounds, indole compounds and aniline compounds increased. Since main compounds in bio-oils were furan-based compounds, furan was used as a model compound in this Example. The decrease of WHSV allowed more sufficient reaction to facilitate the production of products towards the direction of indole, while the increase of WHSV was favorable to produce pyrrole compounds.

TABLE 17

Product selectivities of fixed bed pyrolysis products

| WHSV ($h^{-1}$) | Carbon yield of nitrogen-containing heterocyclic compounds (C %) | Carbon selectivity (C %) Pyridine | Methyl pyridine | Pyrrole | Methyl pyrrole | Indole | Indolizine | Methyl indole | Aniline | Methyl aniline |
|---|---|---|---|---|---|---|---|---|---|---|
| 0.1 | 37 | 2 | 3 | 2 | <1 | 50 | 7 | 6 | 27 | 3 |
| 0.2 | 40 | 2 | 2 | 20 | <1 | 45 | 3 | 5 | 18 | 5 |
| 0.5 | 43 | 1 | 1 | 56 | 9 | 31 | <1 | 3 | <1 | <1 |
| 0.8 | 45 | <1 | <1 | 67 | 22 | 10 | <1 | 1 | <1 | <1 |
| 1 | 45 | <1 | <1 | 72 | 18 | 8 | <1 | <1 | <1 | <1 |
| 1.5 | 50 | <1 | <1 | 80 | 16 | 4 | <1 | <1 | <1 | <1 |
| 2 | 55 | <1 | <1 | 87 | 13 | <1 | <1 | <1 | <1 | <1 |

Example 16

The effect of temperature on the product distribution was investigated mainly by using furan as a model compound in this Example. The conditions for experiments were as follows: catalyst: HZSM-5 (Si/Al=25); catalyst usage amount: 1 g; carrier gas: $NH_3$; carrier gas flow rate: 40 ml/min; and WHSV: 1 $h^{-1}$. The products of this Example mainly included pyridine compounds, pyrrole compounds, aniline compounds and indole compounds. From Table 18, it could be known that as the temperature increased, the selectivities of pyrrole and methylpyrrole decreased and the selectivities of pyridine compounds, indole compounds and aniline compounds increased.

TABLE 18

Product selectivities of fixed bed pyrolysis products

| Temperature (° C.) | Carbon yield of nitrogen-containing heterocyclic compounds (C %) | Carbon selectivity (C %) Pyridine | Methyl pyridine | Pyrrole | Methyl pyrrole | Indole | Indolizine | Methyl indole | Aniline | Methyl aniline |
|---|---|---|---|---|---|---|---|---|---|---|
| 300 | 36 | <1 | <1 | 90 | 10 | <1 | <1 | <1 | <1 | <1 |
| 400 | 39 | <1 | <1 | 86 | 13 | 1 | <1 | <1 | <1 | <1 |
| 500 | 45 | <1 | <1 | 72 | 18 | 8 | <1 | <1 | <1 | <1 |
| 600 | 27 | 2 | 1 | 33 | 8 | 32 | 6 | 8 | 10 | 1 |
| 700 | 21 | 6 | 9 | 14 | 2 | 20 | 2 | 3 | 35 | 9 |

What is claimed is:

1. A method for preparing a nitrogen-containing aromatic compound by catalytic pyrolysis of an organic material, comprising:

feeding an organic material feed and a catalyst to a reactor; and reacting the organic material feed under the catalysis of the catalyst in the presence of a carrier gas and under heating conditions in the reactor, to generate a reaction stream comprising one or more nitrogen-containing aromatic compounds, wherein the carrier gas comprises a mixture of $NH_3$ and inert gas in a molar ratio greater than 1:19;

wherein the nitrogen-containing aromatic compound comprises pyrazine compounds, pyridine compounds, pyrrole compounds, indole compounds, aniline compounds or a combination thereof;

wherein the reaction temperature in the reactor is 300° C. to 800° C., and as the temperature increases, the selectivity towards pyrrole compounds decreases and the selectivity towards indole compounds and aniline compounds increases.

2. The method of claim 1, further comprising:

separating at least a part of the nitrogen-containing aromatic compounds in the reaction stream, to obtain a product stream comprising the separated nitrogen-containing aromatic compounds and a recycle stream; and feeding at least a part of the recycle stream to the reactor.

3. The method of claim 1, wherein the catalyst comprises one or more of a zeolite catalyst, a non-zeolite catalyst, a metal catalyst and/or a metal oxide catalyst.

4. The method of claim 1, wherein the catalyst comprises $\gamma$-$Al_2O_3$, $SiO_2$—$Al_2O_3$, $WO_3/ZrO_2$, $SO_4^{2-}/ZrO_2$, MCM-41, ZK-5, ZSM-23, SSZ-20, β-zeolite, Y-zeolite, ZSM-5 and/or HZ SM-5.

5. The method of claim 1, wherein the catalyst has a $SiO_2/Al_2O_3$ ratio of 15:1 to 200:1.

6. The method of claim 1, wherein the mass ratio of the catalyst to the organic material is 1:100 to 100:1.

7. The method of claim 1, wherein the catalyst comprises a plurality of pores.

8. The method of claim 7, wherein at least about 95% of pores of one or more catalysts have smallest cross-sectional diameters that lie within a first size distribution and a second size distribution; at least 5% of pores have smallest cross-sectional diameters that lie within the first size distribution; at least about 5% of pores have smallest cross-sectional diameters that lie within the second size distribution; and the first size distribution and the second size distribution do not overlap.

9. The method of claim 1, wherein the catalyst contains one or more of the following doping metals: Cu, Mn, Co, Fe, Ni, Zn, Ga, Pt, In, Ru, Rh, Ir, Pt, Pd, Au, Re, Tl and lanthanide metals.

10. The method of claim 9, wherein the doping metal is doped into the catalyst by dry/wet impregnation or ion exchange.

11. The method of claim 1, wherein the carrier gas further comprises an inert gas.

12. The method of claim 1, wherein the organic material comprises a biomass material.

13. The method of claim 12, wherein the organic material comprises agricultural and municipal solid waste, food waste, animal waste, carbohydrates, lignocellulose or a combination thereof.

14. The method of claim 12, wherein the organic material comprises wood, bagasse, bamboo, corn straws, waste paper, rapeseed meal, Jatropha curcas meal, soybean meal, lee, waste proteins, microalgae or a combination thereof.

15. The method of claim 12, wherein the organic material comprises glucose, cellobiose, cellulose, starch, xylose, xylitol, xylan, chitosan, chitin, sucrose, fructose, aqueous glucose solution, furan, methylfuran, 2,5-dimethylfuran, furfural, 5-hydroxymethylfurfural, 5-methylfurfural, γ-valerolactone, bio-oils, water-soluble bio-oils, water-insoluble bio-oils or a combination thereof.

16. The method of claim 1, wherein the nitrogen-containing aromatic compound comprises pyrazine, 2-methylpyrazine, 2,5-dimethylpyrazine, 2,6-dimethylpyrazine, pyridine, 2-methylpyridine, 3-methylpyridine, 4-methylpyridine, dimethylpyridine, pyrrole, 2-methylpyrrole, 3-methylpyrrole, dimethylpyrrole, indole, methylindole, dimethylindole, aniline, o-methylaniline, m-methylaniline, p-methylaniline, dimethylaniline or a combination thereof.

17. The method of claim 1, wherein the organic material is fed into the reactor with a weight hourly space velocity (WHSV) of 0.05 to 10.

18. The method of claim 11, wherein the inert gas is nitrogen or helium.

19. The method of claim 13, wherein the organic material comprises carbohydrates.

* * * * *

UNITED STATES PATENT AND TRADEMARK OFFICE

CERTIFICATE OF CORRECTION

PATENT NO. : 9,975,859 B2
APPLICATION NO. : 15/009499
DATED : May 22, 2018
INVENTOR(S) : Ying Zhang et al.

It is certified that error appears in the above-identified patent and that said Letters Patent is hereby corrected as shown below:

In the Claims

Column 44, Line 57:
"HZ SM-5." should read, --HZSM-5.--.

Signed and Sealed this
Fourth Day of June, 2019

Andrei Iancu
*Director of the United States Patent and Trademark Office*